US011122987B2

(12) United States Patent
Barash et al.

(10) Patent No.: US 11,122,987 B2
(45) Date of Patent: Sep. 21, 2021

(54) METHOD AND SYSTEM FOR RADIOFREQUENCY (RF) TISSUE(S) MONITORING

(71) Applicant: Sensible Medical Innovations Ltd., Netanya (IL)

(72) Inventors: Yiftach Barash, Tel-Aviv (IL); Amir Saroka, Tel-Aviv (IL); Shlomi Bergida, Udim (IL); Nadav Mizrahi, Tel-Aviv (IL)

(73) Assignee: Sensible Medical Innovations Ltd., Netanya (IL)

( * ) Notice: Subject to any disclaimer, the term of this patent is extended or adjusted under 35 U.S.C. 154(b) by 46 days.

(21) Appl. No.: 16/609,750

(22) PCT Filed: Dec. 21, 2017

(86) PCT No.: PCT/IL2017/051375
§ 371 (c)(1),
(2) Date: Oct. 31, 2019

(87) PCT Pub. No.: WO2018/122837
PCT Pub. Date: Jul. 5, 2018

(65) Prior Publication Data
US 2020/0305759 A1   Oct. 1, 2020

Related U.S. Application Data

(60) Provisional application No. 62/439,170, filed on Dec. 27, 2016.

(51) Int. Cl.
*A61B 5/053*  (2021.01)
*A61B 5/0538*  (2021.01)
(Continued)

(52) U.S. Cl.
CPC ............ *A61B 5/0538* (2013.01); *A61B 5/065* (2013.01); *A61B 5/087* (2013.01); *A61B 5/0816* (2013.01);
(Continued)

(58) Field of Classification Search
CPC ......... A61B 5/0538; A61B 5/065; A61B 5/08; A61B 5/0816; A61B 5/087; A61B 5/6823;
(Continued)

(56) References Cited

U.S. PATENT DOCUMENTS 5,785,051 A   7/1998   Lipscher et al.
7,162,296 B2  1/2007   Leonhardt et al.
(Continued)

FOREIGN PATENT DOCUMENTS

WO   WO 2011/141915   11/2011
WO   WO 2018/122837   7/2018

OTHER PUBLICATIONS

International Preliminary Report on Patentability dated Jul. 11, 2019 From the International Bureau of WIPO Re. Application No. PCT/IL2017/051375. (8 Pages).
(Continued)

*Primary Examiner* — Eun Hwa Kim

(57) ABSTRACT

There is provided a system, comprising: internal probe(s) for transmitting and/or receiving an RF signal, the internal probe(s) set to be mounted on an elongated guiding element set for insertion via the pharynx into a tract of a patient, the internal probe(s) and elongated guiding element are configured to be directly inserted into the tract independently of another guiding device; external probe(s) which is set to be positioned in a location outside the body for transmitting and/or receiving an RF signal; a processing unit configured to analyze an RF signal transmitted between transducer(s) of
(Continued)

the internal probe(s) and transducer(s) of the external probe(s), propagating via tissue(s) of the patient between walls of the tract and a skin layer of the patient, to estimate at least one dielectric property of the tissue(s); wherein the RF signals are unsuitable for generating anatomical images of the tissue(s).

41 Claims, 6 Drawing Sheets

(51) Int. Cl.
*A61B 5/06* (2006.01)
*A61B 5/08* (2006.01)
*A61B 5/087* (2006.01)
*A61B 5/00* (2006.01)

(52) U.S. Cl.
CPC ............ *A61B 5/687* (2013.01); *A61B 5/6823* (2013.01); *A61B 5/6852* (2013.01); *A61B 2503/045* (2013.01)

(58) Field of Classification Search
CPC .. A61B 5/6852; A61B 5/687; A61B 2503/045
See application file for complete search history.

(56) References Cited

U.S. PATENT DOCUMENTS

| | | | |
|---|---|---|---|
| 8,226,571 | B2 | 7/2012 | Landesberg et al. |
| 2005/0137480 | A1 | 6/2005 | Alt et al. |
| 2009/0036790 | A1 | 2/2009 | Landesberg et al. |
| 2009/0209849 | A1 | 8/2009 | Rowe et al. |
| 2010/0056907 | A1 | 3/2010 | Rappaport et al. |
| 2010/0256462 | A1 | 10/2010 | Rappaport et al. |
| 2013/0060103 | A1 | 3/2013 | Bergida et al. |
| 2013/0281800 | A1 | 3/2013 | Saroka et al. |
| 2015/0025333 | A1 | 1/2015 | Weinstein et al. |
| 2015/0031979 | A1* | 1/2015 | Rappaport ........... A61B 5/7278 600/407 |

OTHER PUBLICATIONS

International Search Report and the Written Opinion dated Mar. 22, 2018 From the International Searching Authority Re. Application No. PCT/IL2017/051375. (11 Pages).
Reicher et al. "Use of Radio Frequency Identification (RFID) Tags in Bedside Monitoring of Endotracheal Tube Position", Journal of Clinical Monitoring and Computing, 21(3): 155-158, Jun. 2007.
Supplementary European Search Report and the European Search Opinion dated Jul. 31, 2020 From the European Patent Office Re. Application No. 17886657.0.

* cited by examiner

METHOD AND SYSTEM FOR RADIOFREQUENCY (RF) TISSUE(S) MONITORING

RELATED APPLICATIONS

This application is a National Phase of PCT Patent Application No. PCT/IL2017/051375 having International filing date of Dec. 21, 2017, which claims the benefit of priority under 35 USC § 119(e) of U.S. Provisional Patent Application No. 62/439,170 filed on Dec. 27, 2016. The contents of the above applications are all incorporated by reference as if fully set forth herein in their entirety.

FIELD AND BACKGROUND OF THE PRESENT INVENTION

The present invention, in some embodiments thereof, relates to biological tissue monitoring and, more particularly, but not exclusively, to methods and systems of using radiofrequency (RF) signals to estimate parameters of biological tissues.

In monitoring systems, which are based on analysis of EM signals, an EM radiation signal is delivered into the body, propagates therethrough and/or reflected therefrom, and then intercepted and evaluated.

EM based monitoring systems were disclosed, for example, in:

U.S. Patent Application Pub. No. 2010/0056907, filed on Aug. 20, 2009, which describes inter alia a method for monitoring at least one cardiac tissue.

U.S. Patent Application Pub. No. 2010/0256462, filed on Sep. 4, 2008, which teaches among other things a method for monitoring thoracic tissue.

International Patent Application Pub. No. WO20111/141915, filed on May 12, 2011, which teaches for example a system for monitoring biological tissue of a patient of at least 24 hours.

U.S. Pat. No. 5,785,051 which describes "a process for monitoring the position of an endotracheal tube inserted in a patient utilizes an apparatus that comprises first transducer means disposed within the trachea of the patient and second transducer means disposed on the outer skin surface of the patient's neck."

U.S. Pat. No. 7,162,296 which describes "A ventilation system is combined with a measuring method for electric impedance tomography (EIT)."

U.S. Pat. No. 8,226,571 which describes "The method comprises recording signals from a plurality of sensing location on the chest of the subject, at least a portion of the signals being indicative of a local motion of the chest at a respective sensing location."

"Use of radio frequency identification (RFID) tags in bedside monitoring of endotracheal tube position." To reicher et al. J Clin Monit Comput. 2007 June; 21(3):155-8. Epub 2007 Apr. 4, which describes "The use of handheld RFID detectors and RFID tag-labeled endotracheal tubes could allow for easy and accurate bedside monitoring of endotracheal tube position, once initial proper placement is confirmed."

SUMMARY OF THE PRESENT INVENTION

According to a first aspect a system for estimation at least one dielectric property of tissue of a patient, comprises: at least one internal probe for at least one of transmitting and receiving an RF signal, the internal probe set to be mounted on an elongated guiding element set for insertion via the pharynx into a tract of a patient, the internal probe and elongated guiding element are configured to be directly inserted into the tract independently of another guiding device; at least one external probe which is set to be positioned in a location outside the body for at least one of transmitting and receiving an RF signal; a processing unit configured to analyze an RF signal transmitted between at least one transducer of the at least one internal probe and at least one transducer of the at least one external probe, propagating via at least one tissue of the patient between walls of the tract and a skin layer of the patient, to estimate at least one dielectric property of the at least one tissue; wherein the RF signals are unsuitable for generating anatomical images of the at least one tissues.

The systems and methods of some embodiments allow performing real time signal analysis for detecting and/or monitoring dielectric properties and/or dielectric related changes in pulmonary tissues, for instance due to fluid accumulation, with a limited number of transducer(s), without a need for imaging of the thorax or the lung. Detecting the location of the internal probe, migration movement and/or unwanted displacement of the ventilation tube and/or nasogastric tube may be detected. Early detection of tube displacement may allow early repositioning of the tube, which may prevent or reduce medical complications secondary to a misplaced tube.

In a first possible implementation form of the system according to the first aspect as such or according to any of the preceding implementation forms of the first aspect, the system comprises an output unit configured to output the at least one dielectric property.

In a second possible implementation form of the system according to the first aspect as such or according to any of the preceding implementation forms of the first aspect, the output unit is configured to output the at least one dielectric property in a spatial pattern corresponding to an anatomical arrangement of the at least one tissue, the spatial pattern being unsuitable for generating an anatomical image of the at least one tissue.

In a third possible implementation form of the system according to the first aspect as such or according to any of the preceding implementation forms of the first aspect, the tract includes the trachea or esophagus.

In a fourth possible implementation form of the system according to the first aspect as such or according to any of the preceding implementation forms of the first aspect, the at least one internal probe includes insulation material configured to protect the internal probe again damage from body fluids within the tract.

In a fifth possible implementation form of the system according to the first aspect as such or according to any of the preceding implementation forms of the first aspect, the elongated guiding element is a solid rod configured for navigation within the pharynx and the tract.

In a sixth possible implementation form of the system according to the first aspect as such or according to any of the preceding implementation forms of the first aspect, the elongated guiding element including the internal probe has a diameter small enough for insertion into the tract when the tract contains a pre-existing other tube.

In a seventh possible implementation form of the system according to the first aspect as such or according to any of the preceding implementation forms of the first aspect, the processing unit analyses the RF signal to estimate at least one of a fluid content level and a change in the fluid level of the at least one tissue.

In an eighth possible implementation form of the system according to the first aspect as such or according to any of the preceding implementation forms of the first aspect, the processing unit analyses the RF signal to estimate at least one of an air content level and a change in the air level of the at least one tissue.

In a ninth possible implementation form of the system according to the first aspect as such or according to any of the preceding implementation forms of the first aspect, the processing unit analyses the RF signal to estimate migrational movement of the at least one internal probe within the patient tract denoting migrational movement of at least one of an endotracheal tube within the trachea and a nasogastric tube within the stomach.

In a tenth possible implementation form of the system according to the first aspect as such or according to any of the preceding implementation forms of the first aspect, the processing unit analyses the RF signal to detect excess stomach acid in the esophagus.

In a eleventh possible implementation form of the system according to the first aspect as such or according to any of the preceding implementation forms of the first aspect, the system further comprises a ventilation analysis unit for electrical communication with the processing unit and with a ventilation machine programmed to ventilate the patient according to patient ventilation patterns, the ventilation machine generates signals indicative of the patient ventilation patterns, the processing unit correlates the RF signal denoting sensed ventilation patterns with the received patient ventilation patterns, to compare actual ventilation patterns in the patient tissue with desired ventilation patterns programmed for delivery by the ventilation machine.

In a twelfth possible implementation form of the system according to the first aspect as such or according to any of the preceding implementation forms of the first aspect, the system further comprises a mechanical ventilation machine interface for electrical coupling to a mechanical ventilation machine ventilating the patient, the processing unit performing a calibration of RF signals denoting sensed ventilation patterns based on patient ventilation parameters received from the mechanical ventilation machine, the processing unit analyzing the calibrated RF signals for changes in patient ventilation patterns.

In a thirteenth possible implementation form of the system according to the first aspect as such or according to any of the preceding implementation forms of the first aspect, the at least one internal probe includes an antenna and the at least one external probe includes an antenna.

In a fourteenth possible implementation form of the system according to the fourteenth implementation form aspect, one or both antennas are a dipole antenna.

In a fifteenth possible implementation form of the system according to the first aspect as such or according to any of the preceding implementation forms of the first aspect, the RF signal has a frequency between about 300 Megahertz (MHz) and about 10 Gigahertz (GHz).

In a sixteenth possible implementation form of the system according to the first aspect as such or according to any of the preceding implementation forms of the first aspect, the frequency of the RF signal is selected to improve spatial resolution under higher attenuation during propagation from the internal probe positioned in the tract, through the at least one tissue, to the at least one external probe.

In an seventeenth possible implementation form of the system according to the first aspect as such or according to any of the preceding implementation forms of the first aspect, wherein the processing unit analyses the RF signal to assess lung ventilation through the at least one tissue.

In a eighteenth possible implementation form of the system according to the seventeenth implementation form of the first aspect, lung ventilation is assessed for one or both of symmetrical ventilation between the left and right lung, and for adequate ventilation to at least one lung lobe.

In a nineteenth possible implementation form of the system according to the seventeenth implementation form of the first aspect, lung ventilation is individually assessed for different lung lobes based on RF signals traveling through each respective lung lobe.

In a twentieth possible implementation form of the system according to the seventeenth implementation form of the first aspect, the processing unit generates a signal for adjusting a mechanical ventilation machine ventilating the patient based on the assessed lung ventilation, the generated signal transmitted to at least one of a monitor for display to a user and a ventilation controller of the mechanical ventilation machine for automatically adjusting the mechanical ventilation machine.

In a twenty-first possible implementation form of the system according to the first aspect as such or according to any of the preceding implementation forms of the first aspect, the processing unit analyses the RF signal to detect and/or monitor the abnormal presence of air in undesired body locations.

In a twenty-second possible implementation form of the system according to the first aspect as such or according to any of the preceding implementation forms of the first aspect, the processing unit registers the at least one parameter calculated from respective external probes to 2D or 3D images of the at least one tissue during a respiration cycle.

According to a second aspect, a method for estimating at least one biological parameter of tissue of a patient, comprises: positioning at least one internal probe configured for at least one of transmitting and receiving an RF signal, via the pharynx into a tract of a patient, the at least one internal probe set for insertion and retraction from the tract using an elongated guiding element, the internal probe and elongated guiding element are configured to be directly inserted into the tract independently of another guiding device; positioning at least one external probe outside the body of the patient in proximity to a skin layer of the patient, the external probe configured for at least one of transmitting and receiving an RF signal; propagating the RF signal via at least one tissue between at least one transducer of the at least one internal probe and at least one transducer of the at least one external probe, the RF signal propagating via at least one tissue of the patient between walls of the tract and the skin layer of the patient; analyzing the propagated RF signal to estimate at least one biological parameter of the at least one tissue; and outputting the at least one biological parameter; wherein the RF signals are unsuitable for generating anatomical images of the at least one tissues In a first possible implementation form of the method according to the second aspect as such or according to any of the preceding implementation forms of the second aspect, the internal probe is positioned within an esophagus of an intubated patient having an endotracheal tube in the trachea, or wherein the internal probe is positioned within the trachea of a patient having a nasogastric tube positioned within the esophagus.

In a second possible implementation form of the method according to the second aspect as such or according to any of the preceding implementation forms of the second aspect, the internal probe is positioned within an esophagus of a patient having a nasogastric tube positioned within the esophagus, or wherein the internal probe is positioned within the trachea of an intubated patient having an endotracheal tube in the trachea, the internal probe being positioned next to the nasogastric tube or the trachea.

In a third possible implementation form of the method according to the second aspect as such or according to any of the preceding implementation forms of the second aspect, the at least one biological parameter comprises at least one ventilation parameter of the at least one tissue, the method further comprising adjusting a ventilation machine based on the at least one measured ventilation parameter, to reduce or prevent ventilation induced lung injury.

In a fourth possible implementation form of the method according to the second aspect as such or according to any of the preceding implementation forms of the second aspect, the method further comprises detecting migrational movement of at least one of an endotracheal tube and a nasogastric tube within the tract, the migration movement detected based on analysis of the RF signal transmitted and/or received by the at least one internal probe coupled to the endotracheal tube or the nasogastric tube.

In a fifth possible implementation form of the method according to the fourth implementation form of the second aspect, the method further comprises re-adjusting the position of the endotracheal tube to improve patient ventilation.

In a sixth possible implementation form of the method according to the second aspect as such or according to any of the preceding implementation forms of the second aspect, the RF signal is transmitted by the at least one internal probe and received by the at least one external probe.

In a seventh possible implementation form of the method according to the second aspect as such or according to any of the preceding implementation forms of the second aspect, the tract is an esophagus or a trachea.

In an eighth possible implementation form of the method according to the second aspect as such or according to any of the preceding implementation forms of the second aspect, the patient is intubated and mechanically ventilated.

In a ninth possible implementation form of the method according to the second aspect as such or according to any of the preceding implementation forms of the second aspect, the method further comprises removing the at least one internal probe from the tract after a measuring session has been completed.

In a tenth possible implementation form of the method according to the second aspect as such or according to any of the preceding implementation forms of the second aspect, the at least one tissue includes lung tissue.

In an eleventh possible implementation form of the method according to the second aspect as such or according to any of the preceding implementation forms of the second aspect, the patient is a baby less than 12 months old.

In a twelfth possible implementation form of the method according to the second aspect as such or according to any of the preceding implementation forms of the second aspect, the baby is a prematurely born baby.

In a thirteenth possible implementation form of the method according to the second aspect as such or according to any of the preceding implementation forms of the second aspect, the method further comprises calibrating propagation of RF signals between a plurality of the at least one external probe via the at least one tissue with analyzed RF signals between the at least one internal probe and the at least one external probe.

In a fourteenth possible implementation form of the method according to the thirteenth implementation form of the second aspect, the method further comprises monitoring the at least one biological parameter based only on the propagation of RF signals between the plurality of the at least one external probe.

In a fifteenth possible implementation form of the method according to the second aspect as such or according to any of the preceding implementation forms of the second aspect, the at least one internal probe and the at least one external probe are positioned to confine an individual lobe of a lung.

In a sixteenth possible implementation form of the method according to the second aspect as such or according to any of the preceding implementation forms of the second aspect, the method further comprises detecting abnormal levels of at least one of air and water in the at least one tissue.

In a seventeenth possible implementation form of the method according to the sixteenth implementation form of the second aspect, further comprising treating a patient medical condition to correct the abnormal level.

According to a third aspect, a method for monitoring a mechanically ventilated patient, comprises: positioning at least one internal probe within a tract of a patient via the pharynx, using an elongated guiding element, the internal probe configured for at least one of transmitting and receiving an RF signal, the internal probe and elongated guiding element are configured to be directly inserted into the tract independently of another guiding device; positioning at least one external probe in proximity to a skin layer of the patient, the external probe configured for at least one of transmitting and receiving an RF signal; receiving applied ventilation pattern signals from a ventilation analysis unit coupled to a mechanical ventilation machine mechanically ventilating the patient; correlating between the applied ventilation pattern signals and an RF signal propagated via at least one tissue between at least one transducer of the at least one internal probe and at least one transducer of the at least one external probe; analyzing the correlated signal for monitoring at least one ventilation parameter of the patient; and outputting the at least one ventilation parameter.

In a first possible implementation form of the method according to the third aspect as such, the method further comprises adjusting the mechanical ventilation machine ventilating the patient based on the correlated signal.

According to a fourth aspect, a system for estimating at least one ventilation parameter of a mechanically ventilated patient, comprises: at least one internal probe set for insertion into a tract of a patient via the pharynx, the at least one internal probe set to be mounted on a elongated guiding element, the internal probe configured for at least one of transmitting and receiving an RF signal, the internal probe and elongated guiding element are configured to be directly inserted into the tract independently of another guiding device; at least one external probe which is set to be mounted in an external location for receiving a propagated RF signal, the external probe configured for at least one of transmitting and receiving an RF signal; a ventilation analysis unit for receiving applied ventilation pattern signals of a mechanical ventilation machine mechanically ventilating the patient; a processing unit which analyzes a correlation between the applied ventilation pattern signals and an RF signal propagated via at least one tissue between at least one transducer of the at least one internal probe and at least one transducer of the at least one external probe, for monitoring at least one ventilation parameter of the patient; and an output unit which outputs the at least one ventilation parameter.

In a first possible implementation form of the system according to the fourth aspect as such, the processing unit performs a calibration of the propagated RF signals based on the applied ventilation pattern signals, the processing unit analyzing subsequent calibrated RF signals for changes in patient ventilation patterns.

In a second possible implementation form of the system according to the fourth aspect as such or according to any of the preceding implementation forms of the fourth aspect, the processing unit generates a signal for adjusting the mechanical ventilation machine ventilating the patient based on assessed lung ventilation denoted by the at least one ventilation parameter, the generated signal transmitted to at least one of a monitor for display to a user and a ventilation controller of the mechanical ventilation machine for automatically adjusting the mechanical ventilation machine.

According to a fifth aspect, a system for estimation at least one dielectric property of tissue of a patient, comprises: at least one intrabody probe set to be mounted on an elongated guiding element set for reversible cutting free insertion into a lumen of a patient continuous with the pharynx; at least one extrabody probe which is set to be positioned in an extrabody location for receiving a propagated EM signal; and a processing unit configured to analyze an EM signal transmitted between at least one transducer of the at least one intrabody probe and at least one transducer of the at least one extrabody probe, propagating via at least one tissue of the patient between walls of the lumen and a skin layer of the patient, to estimate at least one dielectric property of the at least one tissue.

Unless otherwise defined, all technical and/or scientific terms used herein have the same meaning as commonly understood by one of ordinary skill in the art to which the present invention pertains. Although methods and materials similar or equivalent to those described herein can be used in the practice or testing of embodiments of the present invention, methods and/or materials are described below. In case of conflict, the patent specification, including definitions, will control. In addition, the materials, methods, and examples are illustrative only and are not intended to be necessarily limiting.

Implementation of the method and/or system of embodiments of the present invention can involve performing or completing selected tasks manually, automatically, or a combination thereof. Moreover, according to actual instrumentation and equipment of embodiments of the method and/or system of the present invention, several selected tasks could be implemented by hardware, by software or by firmware or by a combination thereof using an operating system.

For example, hardware for performing selected tasks according to embodiments of the present invention could be implemented as a chip or a circuit. As software, selected tasks according to embodiments of the present invention could be implemented as a plurality of software instructions being executed by a computer using any suitable operating system. In an embodiment of the present invention, one or more tasks according to described embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data.

Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative discussion of embodiments of the present invention. In this regard, the description taken with the drawings makes apparent to those skilled in the art how embodiments of the present invention may be practiced.

In the drawings.

DESCRIPTION OF SPECIFIC EMBODIMENTS OF THE PRESENT INVENTION

Figure 1:
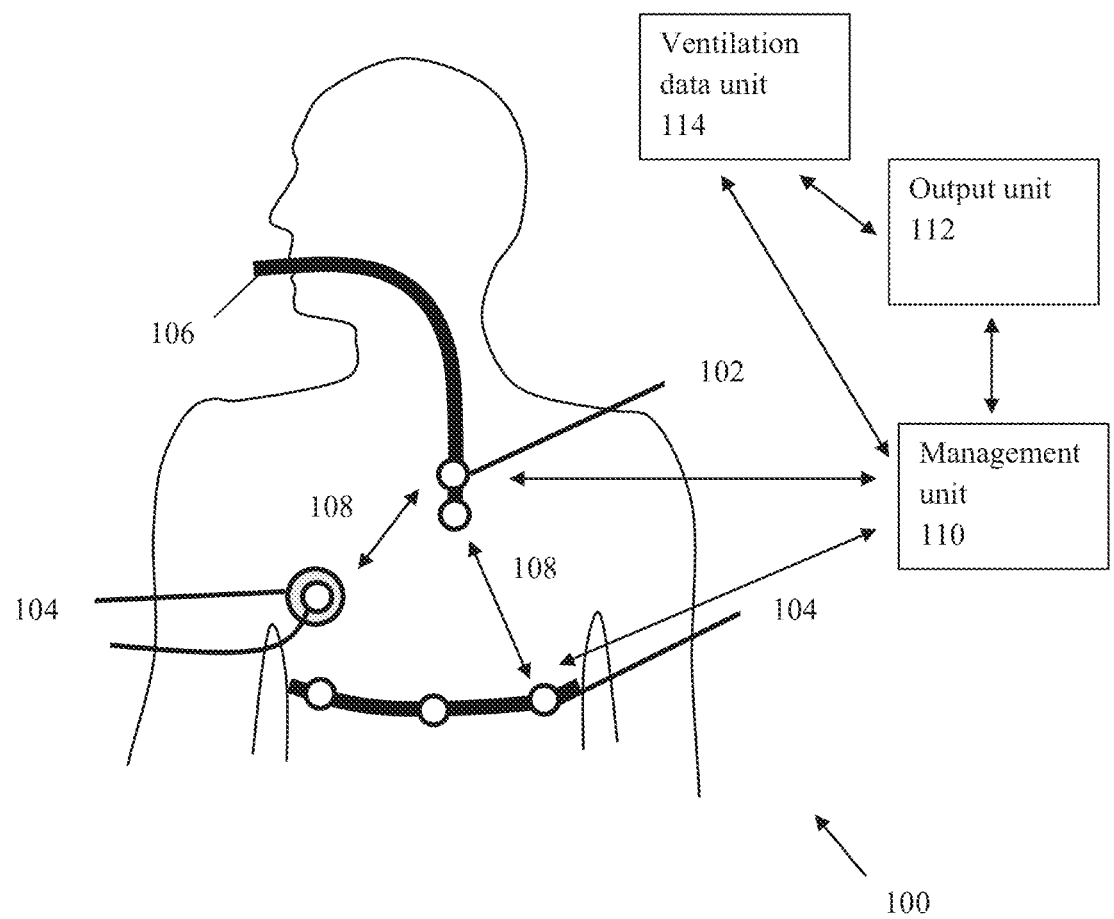
FIG. 1 is a schematic illustration of a monitoring system for monitoring biological parameter(s) of one or more biological tissues according to an EM signal that is propagated between an internal probe(s) and an external probe(s), in accordance with some embodiments.

The present invention, in some embodiments thereof, relates to biological tissue monitoring and, more particularly, but not exclusively, to methods and systems of using RF signals, which may include microware signals, to estimate parameters of biological tissues.

An aspect of some embodiments of the present invention relates to systems and/or methods for monitoring one or more biological parameters of tissues, such as dielectric properties, by analyzing signals propagated between one or more internal transducer(s) and one or more transducer(s) located outside the body of the patient, for example mounted or fixated on the skin tissue of the patient. Such one or more internal transducers may be guided into, and/or fixated (but not implanted) within, an internal operation location within a lumen of a patient. Optionally the lumen includes the gastrointestinal tract and/or the respiratory tract. Optionally, the lumen is continuous with the pharynx, such as the trachea and/or the esophagus. The externally located transducer may be temporarily fixated (e.g. by a patch and/or a wearable belt or garment), and/or hand-held in position, for example, as part of a rod.

As described herein, the term internal probe or internal transducer means a probe or transducer designed to be located inside the patient, for example, within the respiratory and/or gastrointestinal tract. As described herein, the term external probe or external transducer means a probe or transducer designed to be located outside of the body of the patient, for example, in proximity to the skin or contacting the skin.

Optionally, the RF signals suitable for measurement of the dielectric properties of the tissues are unsuitable for performing optical measurements of the tissues. The RF signals are unsuitable for generating anatomical images of the internal tissues of the patient, for example, the way the internal tissues look. The RF signals are unsuitable for acting as an imaging modality. Maps of dielectric property values of the tissues may be reconstructed based on triangulation of the received signals. The measured dielectric values may be registered to a pre-existing anatomical image, for example, obtained from an atlas or image bank.

Optionally, the RF signals are propagated from the transducer(s) which are part of an internal probe guided to be temporarily positioned within the lumen, to transducer(s) of an external probe positioned at the skin or near the skin of the patient. As the internal probe is located in an internal lumen and not on the skin, signal propagation artifacts may be reduced, for example, as compared to propagation of radiofrequency signals between transducer(s) of probes located on or at the skin. For example, an attenuation reduction may be due to a shorter path (where relevant).

The systems and methods of some embodiments allow performing real time signal analysis for detecting and/or monitoring dielectric properties and/or dielectric related changes in pulmonary tissues, for instance due to fluid accumulation, with a limited number of transducer(s), without a need for imaging of the thorax or the lung.

When the internal transducer(s) are located in the trachea or the esophagus, the distance between the transmitting transducers(s) and the receiving transducers(s) is reduced in relation to a pulmonary tissue monitoring system wherein signals are passed between skin transducer positioned on opposite sides of the body (e.g. side to side or front to back). The propagated RF signals from within the body may experience lower attenuation than signals propagated between locations outside the body, which may allow for use of higher frequencies and/or improve spatial resolution.

Optionally, the internal probe is set to be mounted on an elongated guiding element set for reversible cutting free insertion into the lumen of the patient. For example, the internal probe is designed to be connected to a tube (or other probe) for insertion into the patient lumen and/or removal therefrom, without requiring cuts or other surgical intervention, such as an endotracheal tube or a nasogastric tube. In this manner, the internal probe may be quickly, easily and/or minimally invasively be inserted into the patient, and removed after use.

Optionally, the internal probe is configured to be inserted to be inserted within the lumen itself, guided by the elongated guiding element, as described herein.

As used herein, the terms probe and transducer are sometimes used interchangeably, for example, when referring to propagation (e.g., generation and/or reception) of RF waves. The probe includes the transducer. The probe may contain other electrical components and/or containing coupling elements configured to attach to the elongated guiding element.

Optionally, the internal probe is reversibly inserted into the lumen without a cut to the skin (or internal tissues) of the patient. The internal probe may be positioned within the lumen in a non-implanted state, which allows a removal without stitching. Optionally, the internal probe is attached to the guiding element in a manner that prevents the internal probe from being separated from the guiding element while inside the patient. The guiding element guides the internal probe into the patient, maintains the position of the probe while in the patient, and removes the probe from inside the patient. In this manner, the internal probe is not implanted within the patient by the guiding element. The internal probe may be attached and/or removed from the guiding tube outside the patient, for example, by the operator, for example, by screws, a locking mechanism, a clip, or an adhesive. The internal probe may be permanently fixated to the guiding element.

The internal probe may be inserted into the lumen in a minimally invasive manner, using existing body lumens as channels, which may not require surgical intervention. The lumen may be air-filled, and may be temporarily collapsed, such as the esophagus, which may be expanded, for example, by the guiding element. The internal probe may be inserted into the lumen in a non-surgical manner. The internal probe may be removed and/or retracted out of the body, for example, after a calibration procedure and/or after the monitoring process has concluded.

According to some embodiments of the present invention, the internal probe may be coupled to a tube for insertion into the body, such as an endotracheal (or tracheal) tube for insertion into the trachea (e.g., a tube for mechanically ventilating the patient), a nasogastric tube for insertion into the esophagus or stomach (e.g., a tube for delivery of fluids to the stomach or removal of fluids from the stomach), a dedicated catheter for insertion of the internal probe alone or via another tube (e.g., through a channel of the tracheal and/or nasogastric tube), or other tubes. The internal probe may be inserted through the mouth and/or nose into the pharynx and into the trachea and/or esophagus. In such embodiments, analysis of signals to or from the internal probe may be correlated with data from a ventilation machine to monitor resuscitation or a respiration process, and/or correlated with data from the ventilation machine to monitor mechanically assisted air flow in and/or out of the lungs of the patient (e.g., mechanical ventilation). As used herein, the terms respiration machine and ventilation machine may be interchangeable.

Optionally, the fluid content (e.g., air, water, pus, blood, transudate, exudates, or other liquid body fluids) within lungs (or other thoracic tissues, abdominal tissues or body tissues) is measured and/or estimated from analysis of the RF signals. The absolute value of the fluid content may be estimated, measured, and/or changes to the fluid content along a period may be estimated for detecting a trend or a pattern. Measuring and/or monitoring of the fluid content may be performed for different parts of the lungs (e.g., for the lobes). The presence of unwanted fluid may be detected and/or monitored for progression or healing (e.g. reduction of the excess fluid).

Alternatively or additionally, one or more cardiac activity parameters are detected and/or measured based on the analysis of the RF signals, for example, ejection fraction, cardiac output, stroke volume, end diastolic volume, and end systolic volume.

Estimated measurement of the fluid content may detect medical complications, and/or may be used to monitor the progress of medical complications and/or healing. For example, excess fluid content in the lungs may suggest congestive heart failure (CHF), pneumonia (e.g., aspiration pneumonia, pneumonia introduced through the ventilation tube, or other sources). For example, excess fluid (e.g., stomach acid) in the esophagus may suggest acid reflux from the stomach, which may lead to aspiration pneumonia.

Optionally, the internal probe includes a insulation material adapted for insulating the probe against damaging body liquids, such as acids, to protect the probe (e.g., electrical components) from damage by body fluids when located inside the tract of the patient.

Alternatively or additionally, air content within thoracic tissues, abdominal tissues and/or body tissues is estimated, measured and/or monitored from analysis of the RF signals. Optionally, free air content such as air pockets, is estimated, measured and/or monitored in body tissues wherein the presence of free air is abnormal and/or indicative of a medical complication. For example, ventilation (or other causes) may lead to the presence of air in the chest cavity outside the lung (pneumomediastinum), collapse of the lung (pneumothorax), air in the abdomen (pneumoperitoneam), air in between the pericardium wall and the heart (pneumopericardium), and/or air in other undesired locations.

Alternatively or additionally, ventilation within the lungs is estimated, measured and/or monitored from analysis of the RF signals. Ventilation parameters may be estimated, measured and/or monitored, for example, the rate and/or pattern of air entry into the lungs, the rate and/or pattern of air exit from the lungs, the absolute value of air at different points of the respiratory cycle (e.g., peak volume, residual volume), and/or other parameters, for example relating to the kinetics and/or distribution of air in the lungs. The absolute value of the ventilation may be estimated, measured, and/or changes to the ventilation may be estimated. Measuring and/or monitoring of the ventilation may be individually performed for different parts of the lungs (e.g., for the lobes and/or segments thereof). Alternatively or additionally, concentration of air and/or fluid is estimated. The estimated concentration may describe ratio between fluid and air.

The patient may be mechanically ventilated, for example, by an automatic ventilation machine. Measuring the ventilation may be used as feedback to adjust ventilation parameters of the ventilation machine, and/or to generate alerts indicative of the ventilation process, for example in case of problems. The ventilation feedback may be used to adjust the ventilation machine. Optionally this may improve performance of the mechanical ventilation, and/or reduce risk of lung injury, or even to stop ventilation, in some cases. Optionally, ventilation related values calculated by the system are calibrated with actual ventilation provided by the ventilation machine (or other source, for example a spirometer). The calibration may allow the system to monitor the actual ventilation experienced by the patient as estimated and/or measured, and to compare the estimated and/or measured ventilation to the values of the ventilation provided by the mechanical ventilation machine, which represent desired ventilation values. Deviation between the actual and desired ventilation values may be identified, analyzed, and/or outputted. Optionally, a warning indicative of a ventilation problem is given, for example, upon detection of ventilation patterns suggestive of obstructive apnea (not enough air into the lungs), a leak in the tube, a pneumothorax, or other complications.

Optionally, the location of the internal transducer coupled to the tube or probe inserted into the lumen of the patient (e.g., endotracheal tube and/or nasogastric tube) is detected and/or monitored based on the RF signals.

Endotracheal tube location may be detected based on detection of the position of the corresponding internal transducer, for example, based on change in ventilation patterns (e.g., sudden decreased in ventilation in one lung may suggest that the tube is not properly positioned to ventilate that lung). Optionally, changes in the ventilation distribution and/or ventilation spatial pattern indicative of movements of the internal probe (and related transducer) may be detected.

Endotracheal and/or nasogastric tube location may be detected based on detection of the position of the corresponding internal transducer, for example, based on changes to the RF signals (e.g., longer or shorter time of flight of the RF signal between probes may suggest movement of the internal probe). The body effect on the RF signals may be cancelled as part of the signal processing. Optionally, different frequency bands are used for estimating the location of the internal probe and for estimation of biological parameters (e.g., ventilation, fluid level, or others). Alternatively or additionally, the same frequency bands may be used. Optionally, an unexpected change in the signals used to locate the position of the internal probe may indicate that the tube may have shifted position and a warning may be issued accordingly.

In this manner of detecting the location of the internal probe, migration movement and/or unwanted displacement of the ventilation tube and/or nasogastric tube may be detected. Early detection of tube displacement may allow early repositioning of the tube, which may prevent or reduce medical complications secondary to a misplaced tube. As used herein, the phrase biological parameter may sometimes also include parameters indicative of internal probe position, which may denote tube position, as described herein.

An aspect of some embodiments of the present invention relates to systems and/or methods for monitoring a mechanically ventilated patient. The method and/or systems receive applied ventilation pattern signals from a ventilation analysis unit coupled to a mechanical ventilation machine mechanically ventilating the patient. Optionally, the received applied ventilation pattern signals are correlated and/or compared with the measured RF signal (described herein). Optionally, a correlated signal is analyzed for monitoring ventilation parameter(s) of the patient (as described herein), and optionally outputting the ventilation parameter(s). In this manner, the system and/or method may compare the programmed ventilation pattern of the machine, with the actual delivery of air to the patient. Optionally, a calibration is performed between the received applied ventilation patterns and the measured RF signals, to establish a baseline for further measurements. The calibrated RF signals may be used to monitor patient ventilation, optionally without comparison to ventilation parameters provided by the machine. As will be described in greater detail, the calibration and/or correlation may help determine when the patient lungs are properly ventilated. Optionally, ventilation parameter(s) output is used to adjust the ventilation machine manually and/or automatically, such as to achieve desired ventilation goals, as described herein.

Before explaining at least one embodiment of the present invention in detail, it is to be understood that the present invention is not necessarily limited in its application to the details of construction and the arrangement of the components and/or methods set forth in the following description and/or illustrated in the drawings and/or the Examples. The present invention is capable of other embodiments or of being practiced or carried out in various ways.

Reference is now made to FIG. 1, which is a schematic illustration of a monitoring system 100 for monitoring and/or estimating biological parameters(s) of one or more biological tissues according to an RF signal that propagated between one or more internal probes 102, such as an antenna, an RF signal modulating element, and/or an internal element, located within a lumen of the patient, and one or more external probes 104, which are optionally placed on or in proximity to the skin of a patient, in accordance with some embodiments of the present invention.

Optionally, internal probe(s) 102 includes a transducer for transmitting and/or receiving RF signals. Optionally, external probe(s) 104 includes a transducer for transmitting and/or receiving RF signals. As used herein, the terms probe and transducer may be interchangeable, for example, when referring to RF signal transmission and/or reception.

Each transducer (of internal probe 102 and/or external probe 104) may include one or more antennas. The antenna(s) may be connected to a radiofrequency (RF) module. The RF module may include one or more RF signal generators and/or one or more RF signal receivers. Multiple antennas may be connected to multiple RF modules or to one RF module (e.g., with a switch configured to select between connections). The internal probe may be wirelessly connected, and/or connected by a wire guided to an external device. For example, an RF guiding cable may connect an internal probe with an RF module or part thereof positioned outside the body.

Optionally, generation of the RF signal within the patient by the internal probe 102 and reception of the signal at the skin or in proximity to the skin by external probe 104 reduces RF signal scatter by the skin, as may occur when an RF signal is generated at the skin or in proximity to the skin. The attenuation experienced by an RF signal passing through a section of tissue selectively targeted for measurement, is normally lower relative to an RF signal passing through the same tissue section (or nearby tissue) between two externally located probes, as the signal path may be shorter. In this manner, the RF signals generated by system 100 may be more accurate, require less energy and/or provide for higher spatial resolution than signals generated by a system using only transducers placed outside the body of the patient (to measure within corresponding tissues). External sensors (e.g., two neighboring sensors) may suffer from poor isolation between them, having highly conductive external-to-body radiation paths between the external sensors. The internal transducer of probe 102 is better isolated than an external transducer due to its absorbing surrounding, which may reduce crosstalk signals and/or reduce the number of paths through which the energy would be transmitted between the transmitting probe(s) and receiving probe(s). In addition, less attenuation is expected when measuring a transmission between an internal probe and two external probes on opposite sides of the body, than is expected in case of transmission between said two external probes). Regions of the body, such as certain portions of the lung, may be individually and/or selectively monitored by system 100, for example, as compared to RF signal propagation between external probes. For example, the upper lobe and lower lobe of the lungs (left and/or right) may be separately and/or individually monitored. For example, the right middle lobe may be individually monitored separately from the right upper and/or right lower lobes. Portions of the lobes may be individually monitored. The individual monitoring may be performed by selectively placing the internal probe 102 within the lumen of the patient and the external probe 104 at certain locations on the skin (or proximal to the skin) of the patient, so that the part of the lung being monitored is confined between internal probe 102 and external probe 104. System 100 includes internal probe 102 that may provide for measurements that might not be possible or would be difficult using only external probes, such as by reducing RF signal attenuation. For example, measuring RF signal propagation across the patient (e.g., left to right) may be enabled by the internal probe. RF signals directly crossing both lungs (e.g., from left to right) may suffer from excessive attenuation, such as when propagating between two external RF probes. Using an internal probe(s) between the two external probes is capable of breaking the long path to two shorter ones, each causing much less attenuation than the whole path. In a similar manner, system 100 may be used to monitor, estimate and/or measure other parts of the body, such as the thorax, tissues within the thorax, abdomen, esophagus, and/or other tissues.

Internal probe 102 is not surgically implanted within the patient. Internal probe 102 may be positioned in a cutting free manner. Optionally, internal probe 102 is introduced into the patient via existing anatomical routes (or surgically created routes), for example, through the nose, through the nose, and/or through a surgical incision created by a tracheotomy. Internal probe 102 is reversibly positioned in the patient. Internal probe 102 may be easily removed from the patient. The location of internal probe 102 within the lumen may be adjusted, deeper into the patient and/or towards the outside.

Optionally, internal probe 102 is inserted into a lumen (e.g., a hollow lumen or even an air-filled lumen) of the patient, such as the trachea and/or esophagus. Optionally, internal probe 102 is set to be mounted on an elongated guiding element. Optionally, internal probe 102 and/or the elongated guiding element are designed for reversible insertion into the lumen, for example, being sized and/or shaped for insertion into the patient lumen and/or removal out of the patient lumen. For example, internal probe 102 is small enough to be coupled to an endotracheal and/or nasogastric tube for insertion into the trachea and/or esophagus together with the respective tube. For example, internal probe 102 includes a material (e.g., external covering) that provides for coupling to the tube, such as an adhesive, or other materials that are resistant to coupling methods and/or provide for using manufacturing methods for coupling probe 102 to the tube.

Optionally, internal probe 102 is coupled to an elongated guiding element, such as a tube 106, rod or other guiding element inserted into the lumen.

Optionally, probe 102 and/or tube 106 are configured to be directly inserted into the lumen of the patient. Tube 106 may be a solid rod without a hollow interior. Probe 102 and/or tube 106 may be sized for inserted through the nose and/or mouth. Probe 102 and/or tube 106 may be made out of a rigid and/or flexible material to allow navigation into the correct lumen (for example, esophagus or trachea) and/or to allow maneuvering around bends (for example, the pharynx connecting the mouth and esophagus and/or trachea). Probe 102 and/or tube 106 may be made out of, or covered with, insulation materials selected for protection against the damaging lumen environment, for example, to resist and/or protect against stomach acid. Internal probe 102 and/or tube 106 may be inserted independently of another guiding device, such as another guiding sheath. Alternatively, internal probe 102 and/or tube 106 may be guided, for example, by an external sheath, which may then be removed once internal probe and/or tube 106 have been placed in position.

Optionally, tube 106 with attached probe 102 is guided into an unoccupied patient lumen that does not contain another pre-existing tube. For example, when the patient is ventilated through the mouth, tube 106 may be guided through the nose into the esophagus. In another example, when the patient has a feeding tube extending from the nose to the stomach, tube 106 may be guided through the mouth into the trachea.

Alternatively, tube 106 with attached probe 102 is guided into an occupied patient lumen containing another pre-existing tube, for example, an endotracheal tube in the trachea, and/or a nasogastric tube in the esophagus. Tube 106 and/or probe 102 may be configured to be inserted into the lumen independently of the other tube. The diameter of tube 106 and/or probe 102 may be small enough to be inserted into the lumen when the other tube is already located within the lumen, for example, beside the other tube. The diameter may be, for example, no larger than about 1 millimeter (mm), or about 3 mm, or about 5 mm, or about 7 mm, or other intermediate or larger sizes.

Alternatively, tube 106 may be a tube inserted into the lumen of the patient as part of a medical procedure, for example, a tracheal tube and/or endotracheal tube inserted into the trachea to ventilate the patient, a nasogastric tube inserted into the stomach of the patient to introduce and/or remove fluids, or other tubes. Tube 106 may be a dedicated tube, elongated guiding element, or probe (with or without a hollow lumen), for example, inserted through a lumen of an existing positioned tracheal tube, and/or inserted alone. In this manner, internal probe 102 may be introduced and/or removed together with the tube 106, for example, when internal probe 102 is used to monitor tissues of the patient during treatment using the tube 106, such as monitoring for complications of artificial respiration. Verification of correct positioning of tube 106 (e.g., by x-ray or other methods) may provide a basis for verification of correct positioning of internal probe 102 within the hollow lumen. As will be described below, internal probe 102 may be used to monitor the position of tube 106 within the lumen of the patient, and/or to guide initial positioning of tube 106 and/or to guide or monitor the extraction of tube 106.

Tube 106 and/or internal probe 102 may be available in different sizes for insertion into lumens of different sized patients, for example, sized for insertion into a premature infant, into a newborn infant, into a neonate, into a toddler, into a child, into a teenager, into an adult, and/or into normal sized, smaller and/or larger patient variations of the patients.

Internal probe 102 may be coupled to tube 106 using suitable methods, for example, integrated with the tube wall, glued or bonded to the inner or outer tube wall, attached using one or more connectors or other methods.

The location of internal probe 102 within the patient lumen may be set by positioning tube 106 at a given location thereby positioning internal probe 102 at a position that is determined by the position of internal probe 102 along tube 106. Optionally, internal probe 102 is selected to be positioned above the carina, approximately in the center between both lungs. Internal probe 102 may be located at the distal end region of tube 106.

At least one of internal probe 102 and external probe 104 includes a transmitter, and at least one of internal probe 102 and external probe 104 includes a receiver thereby allowing transmission and reception of RF in at least one direction. The direction of transmission may be from internal probe 102 to external probe 104. Alternatively, the direction of transmission may be from external probe 104 to internal probe 102. Alternatively, transmission may occur in both directions, between internal probe 102 and external probe 104. Numeral 108 depicts an example of a path of an RF signal that is propagated from internal probe 102 to external probe 104, and/or from external probe 104 to internal probe 102.

Optionally, internal probe 102 includes a transmitter and external probe 104 includes a receiver. For example, internal probe 102 includes a radiofrequency (RF) and/or microwave (MW) transmitter, and external probe 104 includes a RF and/or MW receiver. Optionally, both of probes 102, 104 include transceivers (as a single module or as separate receiver and transmitter). Optionally, only internal probe 102 sends the RF signal, and only external probe 104 receives the RF signal. Alternatively, both internal probe 102 and external probe 104 can both transmit and receive RF signals. Optionally, internal probe 102 transmits to external probe 104, and receives a reflected signal back from external probe 104 and/or another signal generated in response to the received signal, and/or another signal generated independently by external probe 104. Alternatively or additionally, transmission occurs between external probes 104, without involvement of internal probe 102, for example, as described below in more detail. Optionally one of internal probe 102 and external probe 104 includes only a receiver or a transmitter, such that probe 102 and/or 104 may only receive or transmit an RF signal, while the other of internal probe 102 and external probe 104 includes both a transmitter and a receiver, and is able to both transmit and receive signals Optionally, internal probe 102 and/or external probe 104 comprise antennas, such as dipole antennas. The type and shape of the internal antenna may be selected based on the lumen in which the antenna will be inserted. The internal antenna may be a loop antenna shaped and/or placed to fit within the lumen. The internal antenna may be a dipole shaped antenna, which may be placed along the wall of the lumen. Other shapes may be selected, for example, a spiral antenna may be adapted to match the lumen shape. The antenna may be designed to be agnostic to near antenna environment based on increasing electrical distance using high dielectric components, and/or electrical design for agnostic antenna, or other considerations. Some useful probes are described, for example, in International Patent Applications Publication Numbers WO2013/105085 and/or WO2012059929 which are incorporated herein by reference.

Optionally, the RF signal has a frequency between about 300 Megahertz (MHz) and about 10 Gigahertz (GHz). Optionally, the RF signal is a microwave signal. Optionally, the frequency of the RF signal is selected for propagation from the internal probe positioned in the lumen, through the tissue, to the external probe. As the attenuation of the RF is relatively lower as described above (e.g., due to the internal to external direction), the frequency of the RF signal may be selected to be relatively higher than the frequency of an RF signal generated and transmitted only between external probes through the tissue, and/or transmitted from the external probe to the internal probe. The higher frequencies may provide for improved spatial separation. For example, frequencies or frequency bands selected within a range of 2 GHz-30 GHz may be used, or even 4 GHz to 10 GHz or 18 GHz to 26 GHz may be used in some cases.

Optionally, external probe 104 is set to be mounted in an external location for receiving the propagated RF signal, such as at or near a skin layer of the patient. External probe 104 may be attached to the patient's body using a sticker, a patch, or a designated attachment unit and/or placement unit, for example as described in International Patent Applications Publication Numbers WO2013/164837 which are incorporated herein by reference. External probe 104 may be integrated into a garment, a belt, a strap, a vest, a piece of cloth, and/or into another device that is positioned on the patient's body, for example, as described with reference to International Patent Applications Publication Number WO2013/093923 which is incorporated herein by reference. External probe 104 may be optionally attached to the patient's skin using an adhesive. External probe 104 may be attached for the entire duration of a monitoring period or it may be removed and replaced once or several times during that period.

External probe 104 may be placed in proximity to the body of the patient, for example positioned in or on a mattress, a bed frame, on a wall in the patient's home and/or a chair. For example external probe 104 may be a handheld device that is held interchangeably in proximity to the body of the patient or a device incorporated into a patient's bed. In such an embodiment, the monitored patient has just to stand, sit, or lie next to external probe 104, and to initiate the monitoring session without having to wear or attach external probe 104. Optionally, different external probes 104 may be used interchangeably, for example based on the proximity of the patient thereto, or convenience.

It should be noted that although only one external probe 104 and one internal probe 102 are described herein, any number of external probes 104 and/or internal probes 102 may be used, interchangeably or simultaneously or in sequence. The probes may be adapted to transmit and/or intercept a plurality of RF signals in a plurality of continuous or intermittent sessions during a monitoring period which may be longer than 1, 2, 4, 8, 12, 16, 20 and 24 hours, days, weeks, months, and/or years, in which the patient may be ambulatory and/or in a monitoring position. Alternatively, a single session is held to estimate and/or measure parameters of tissue, without additional monitoring sessions at different periods of time.

Optionally, external probe 104 and/or internal probe 102 communicate with a management unit 110, optionally via a wireless and/or wired connection, for example, as further described below.

Optionally, management unit 110 communicates with an external ventilation data unit 114 for receiving and/or providing ventilation related data. For example, ventilation data unit 114 is part of or associated with a ventilation machine artificially ventilating the patient via endotracheal tube 106.

Optionally, management unit 110 communicates with an output unit 112 for outputting the estimated biological parameter. Unit 112 may be, for example, a device for displaying the estimated biological parameter to the user, for example, a screen, a flashing light, or other devices to indicate the values. Unit 112 may be, for example, a unit to generate signals indicative of the estimated biological parameter in a format suitable for reception by an external device, such as ventilation machine 114, an external server, or other devices. The output may be used to adjust machine 114. The output may be stored in a repository.

Figure 2:
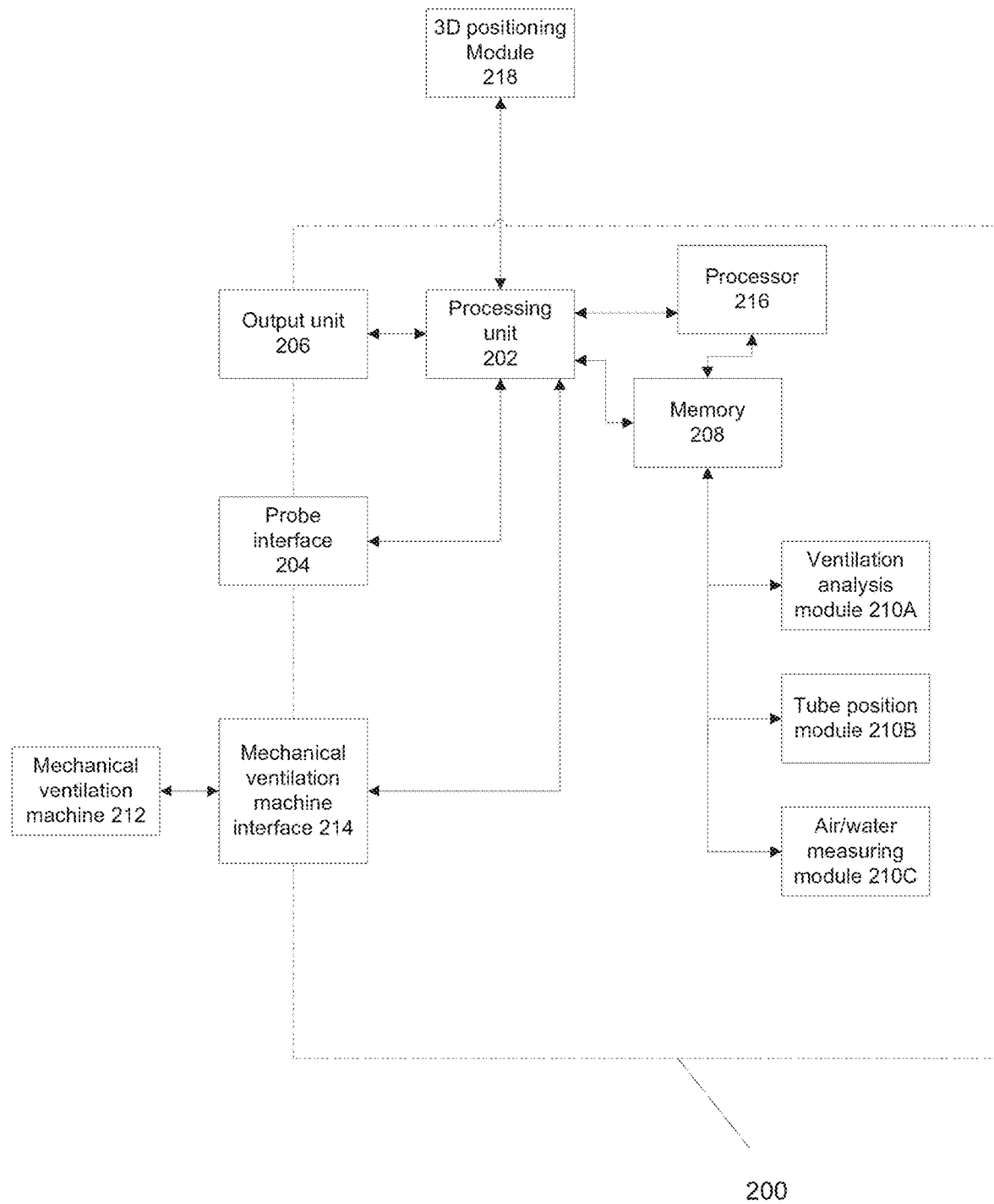
FIG. 2 is a schematic illustration of a management unit for monitoring biological parameter(s) of one or more biological tissues, in accordance with some embodiments.

Reference is now made to FIG. 2, which is a schematic block diagram of a management unit 200 configured to perform processing and/or functions of a monitoring system based on RF signals traveling through at least one tissue, in accordance with some embodiments of the present invention. The RF signals may be generated within a body lumen and received at the skin of the patient or in proximity to the skin after traveling through the tissue, and/or the RF signals may be generated outside the body of the patient and received within the body lumen after traveling through the tissue. Optionally, management unit 200 is or comprises management unit 110 of system 100, as described with reference to FIG. 1.

Management unit 200 provides processing functionality, for example, analysis of patient ventilation (i.e., for artificially ventilated patients), monitoring of positioning and/or movement of tube 106 (e.g., endotracheal and/or nasogastric tube), detection and/or monitoring of water and/or fluid levels in tissues, detection and/or monitoring of free air levels in tissues, detection and/or monitoring complications of patient ventilation, detection of tumors within the tissue, and/or other functionality.

Optionally, control unit 200 includes a processor 216 and a memory 208 having one or more modules and/or data repositories stored thereon for execution by processor 216. Optionally, memory 208 is in electrical communication with processing unit 202.

At least one of the probes 102, 104 includes or communicates with a processing unit 202 (e.g., part of management unit 200) which analyses and/or measures the propagated RF signals to estimate one or more biological parameters of the one or more tissues which are placed between the probes 102, 104, for example as further described below. Processing unit 202 may utilize modules described herein (or other modules) to perform processing functions, such as modules 210A-C. Probes 102 and/or 104 may communicate with management unit 200 through probe interface 204. Communication may be wired and/or wireless.

Optionally, processing unit 202 estimates relative or absolute values of the biological parameters, for example, estimated water content, estimated air content, estimated free air content, estimated ventilation, estimated tube position (and/or position of the internal probe), heart related changes, or other parameters. Alternatively or additionally, processing unit 202 estimates changes in the values of the biological parameters, for example, changes over time, such as changes in water content, changes in air content, changes in ventilation, changes related to heart functionality like heart movement, ejection fraction, changes in tube position or other changes.

Optionally, system 100 and/or control unit 200 detect and/or monitor patient ventilation, for example, by a ventilation analysis module 210A and/or processing unit 202. The patient may be artificially ventilated through tube 106, automatically by a ventilation machine 212 and/or manually by a healthcare provider such as using a hand-held bag valve mask. The air flow in and out of the lungs may be estimated. The air actually reaching lung tissue (i.e., alveolar ventilation) may be estimated. Peak air volume and/or residual air volume may be estimated.

System 100 and/or control unit 200 may detect adequate or inadequate ventilation. A notification may be provided, for example an alarm may be raised when ventilation is inadequate, for example, through output unit 206 such as with a red blinking light, a siren, a screen, or other methods. Data of the estimated ventilation may be used to control and/or adjust ventilation machine 212, for example, through a mechanical ventilation interface 214.

Optionally, system 100 and/or control unit 200 is in electrical communication with a 3D positioning module 218. Module 218 may be an external stand-alone system, and/or may be integrated within system 100 and/or control unit 200. 3D positioning module 218 performs 3D X-Y-Z positioning of the internal probe and/or external probe coupled to control unit 200. 3D positioning system 218 may perform calibration of the patient anatomy, for measuring and/or estimating absolute values. 3D positioning system 218 may calculate data for presentation of the measured and/or estimated values based on the corresponding locations of the measured and/or estimated values. The frequency bands used by 3D positioning system 218 may be similar and/or different than the frequency bands used by system 100. The position sensors used by 3D positioning system 218 may be similar and/or different than the sensors used by system 100. For example, the tags may be about 2-3 millimeters (mm) in size.

Optionally, ventilation analysis module 210A analyses the RF signals in calibration with applied patient ventilation patterns, such as how ventilation machine 212 is ventilating the patient, for example, the pressure and/or volume and/or other parameters of ventilation provided by machine 212. The ventilation patterns may be received from ventilation machine 212 through mechanical ventilation interface 214. Calibration of the RF signals with the received applied ventilation patterns may be used to detect complications of ventilation. Mismatches between the received applied ventilation patterns (provided by machine 212) and the measured RF-based ventilation patterns may be identified and/or notification (e.g. alerts) may be given. For example, when machine 212 is pushing air into the patient, RF signals may be used to estimate ventilated air in the lungs. Inadequate air ventilation during this time period may suggest a ventilation problem, such as a collapsed lung, improperly placed endotracheal tube, or other problems. Optionally, the volume in different lung lobes may be estimated over time. Optionally, a trend is determined.

Optionally, ventilation measurements and/or estimates (based on the RF signals) are calibrated with data received from the ventilation machine (or other devices) denoting the respiration cycle. In this manner, the RF-based measured ventilation parameters may be correlated with corresponding inhalation, exhalation, air entry, air exit, and/or other portions of the respiratory cycle.

Optionally, ventilation is assessed for different lungs lobes, optionally independently. For example, ventilation is separately estimated for the left upper lobe (LUL), left lower lobe (LLL), right upper lobe (RUL), right lower lobe (RLL), and/or right middle lobe (RML).

Optionally, ventilation is detected and/or monitored, and symmetry is optionally desired. Examples for symmetry include, approximately symmetrical ventilation (e.g., air entry and/or air exit) to the left and right lungs as a whole, approximately symmetrical ventilation to the different lobes, or other ventilation comparisons. Asymmetrical ventilation (e.g., within a tolerance range) may be detected. Early detection of asymmetrical ventilation may prevent complications, such as over inflation of a lung (or lobe) and/or under inflation of a lung (or lobe), which may lead to lung injury, or even pneumonia, and/or suggest existing injury.

Optionally, processed ventilation patterns are provided as a generated signal for adjusting the mechanical ventilation machine 212, ventilating the patient based on the assessed lung ventilation. The generated signal may transmitted to a monitor for display to a user (e.g., through output unit 206) and/or a ventilation controller of the mechanical ventilation machine 212 for automatically adjusting the mechanical ventilation machine (e.g., through mechanical ventilation interface 214).

Optionally, multiple ventilation measurements and/or estimates are collected from different parts of the lungs. The multiple estimates may be overlaid on, and/or displayed as corresponding 2D or 3D image(s) or other representation of the lungs and/or thorax (e.g., rendered image, x-ray of the patient, general model, 2D or 3D arrangement of values).

Optionally, the estimates are registered and/or overlaid on images denoting the respiratory cycle, such as inhalation and/or exhalation. The measurements registered and/or overlaid on respiratory images may be displayed as a video denoting patient breathing. The splice may be axial, coronal, sagittal, or in other planes, depending on the relative positioning of external probes 104 around the patient. In this manner, a user may quickly spot problematic regions, for example, areas of poor ventilation during the respiratory cycle, for example, by visually noticing regions of the lung that do not have proper air entry and/or air exit during the respective portions of the ventilation and/or respiratory cycle. The measurements may reflect transient volume changes for different lung regions.

Optionally, the estimates and/or measurements of the biological parameters (e.g., dielectric property) are provided in a spatial pattern. The spatial pattern may be unsuitable for generation of anatomical images depicting the physical layout of the interior tissues or organs of the patient. Optionally, the spatial pattern corresponds to the anatomy of the monitored tissue of the patient. The RF signals traveling through different tissue portions may be correlated with the physical location of the tissue portions to generate the spatial pattern. The spatial pattern may be displayed in a 2D or 3D arrangement corresponding to the anatomy of the patient, and/or overlaid on a 2D and/or 3D image. In this manner, measurements and/or estimates by different RF signals may be easily identified with the corresponding tissues. For example, estimates of fluid levels and/or ventilation parameters may be provided for different locations of the lungs that were measured. The spatial arrangement may help determine abnormal estimates, which may reside within normal values, such as parts of the lung that have accumulated fluid and/or inadequate ventilation.

Optionally, trends in lung ventilation (e.g., lobar ventilation) may be analyzed to optimize ventilation parameters.

It is noted that tumors or other abnormalities may be detected by system 100 and/or unit 200, for example, asymmetrical RF signal readings between the left and right lungs in certain regions (e.g., while surrounding regions provide symmetrical RF signal readings, and while taking into account natural asymmetry, such as that which is due to the position of the heart and to the difference between lungs) may suggest the presence of a tumor or other abnormal lung structure, such as fibrotic regions, cavitation region, or other abnormal structures.

The analysis of the propagated RF signals detects, estimates and/or measures dielectric related properties and/or dielectric related property changes of the tissue(s), for example as described in International Patent Application Pub. No WO 2010/100649, International Patent Application Pub. No WO 2009/031150, and/or International Patent Application Pub. No 2009/031149, which are incorporated herein by reference. The dielectric property may be indicative of fluid content in the lung. As used herein, a biological parameter means any one or more values of biological indicators which reflect a property of one or more organs and/or tissues, for example fluid level in a tissue, the size and/or type of a tumor, mechanical movements of an organ, dielectric related properties of a tissue and changes thereof and the like. Optionally, a biological parameter may be a trend for example the values of one or more estimated biological parameters over time. As used herein, a dielectric related property of a specific volume, organ, or tissue includes one or more of magnetic permeability, electric permittivity and conductivity of the composite material within a specific volume. Such a dielectric related property may be affected by presence or distribution of fluid, concentration of substances, in the fluid in the internal tissue and/or organ, the ratio of fibrotic tissue, a concentration of inflammatory substance in the fluid in the internal tissue and/or organ and physical configuration of organs or tissues of different properties in the volume measured. As used herein, a dielectric related property change is optionally a change that is indicative of a change in one or more dielectric related properties and/or in the configuration of internal tissues or in an internal lumen between tissues. For example, in case of a fluid change in the internal lumen, such as when blood fills the tissue parenchyma, a change in the dielectric coefficient of the region is expected. In another example, an ischemic region within a tissue may change its dielectric related properties to fibrotic tissue reflected by a change in dielectric coefficient (e.g., a higher dielectric constant for fibrotic lung tissue as compared to healthy lung tissue). In another example, a region may change dielectric related properties as a result of a cancerous tumor within a region growing in size or becoming more vascularized.

Optionally, the processing unit calculates a dielectric related property or a dielectric related property change by analyzing changes in the propagated RF signals in a number of RF signal transmission sessions and over a monitoring period.

The biological parameter may be determined based on a combination between the dielectric related properties and optionally also additional data, for example, ventilation, and/or geometrical data estimated and/or measured by internal and/or external devices. Optionally, the biological parameter may be determined based on a combination between the dielectric related properties and user related data from external sources and/or sensors, for example, applied ventilation data generated by a mechanical ventilation machine.

Control unit 200 and/or processing unit 202 and/or components thereof may be located in an external management unit 110, for example as exemplified in FIG. 1, or in any of the probes. Optionally, unit 200 includes an output port and/or is connected to an output unit 206 which outputs, for example transmits or presents the detected parameters. For example, the output unit 206 may include a transmitter, for wirelessly transmitting the change to a central monitoring server. In another example, the output unit includes a screen for presenting data, for example an estimated parameter. Additionally or alternatively, the biological parameter is optionally recorded in a repository, for example, a flash memory unit. It should be noted, that the term processing unit may mean herein a local processing unit, a distributed processing unit, and/or a remote processing unit. In an embodiment in which the processing unit is remote, the data which is forwarded to the processing unit may be transmitted by wired or wireless communication to the remote processing unit for remote processing. Optionally, the processing unit may include algorithms that may mitigate artifacts and/or noise that may reduce the quality of the measurements performed by the apparatus, and/or reduce or cancel the effect of posture changes (e.g., based on external 3D x-y-z position data measured by 3D position module 218), and/or perform and/or analyze measurements based on posture. For example, these algorithms may include algorithms used to mitigate effects of internal and/or external body movements and/or posture changes effects, for example registration based algorithms, for example, as detailed in International Patent Application Pub. No WO 2010/100649, International Patent Application Pub. No WO 2009/031150, and/or International Patent Application Pub. No 2009/031149.

Optionally, system 100 and/or unit 200 detect and/or monitor the relative position of tube 106 within the patient, for example, by tube position module 210B and/or processing unit 202. The position may be monitored based on an internal probe(s) 102 coupled to tube 106, for example, to the distal end region of a tube 106 inserted within the patient. In this manner, detection of movement of tube 106 may be estimated indirectly, based on detection of movement of internal probe 102 coupled to tube 106. For example, migrational movement of tube 106 within the lumen, either deeper into the patient and/or in an outward bound direction (e.g., towards the mouth of the patient) and/or in any other direction (e.g., an undesired direction), may be detected. Such movement may be detected before causing injury or other complications to the patient, such as asymmetrical ventilation, and/or retraction of the distal end of a nasogastric tube out of the stomach, which may lead to failure to drain stomach contents. Optionally, such movement may be detected before a caused injury or other complications to the patient may be otherwise detected, thereby potentially reducing harm to the patient, if not preventing it completely.

Tube 106 movement may be detected by suitable signal analysis methods, for example, increased or decreased time of flight between internal probe 102 and external probe 104, phase changes in the signal, or changes in other parameters caused by changes in distance (increased or decreased) between probes 102 and 104 from the movement of tube 106. The biological parameters may be analyzed to detect the tube movement.

Optionally, tube 106 is initially positioned manually, and then changes in the initial position are automatically monitored by system 100, for example, based on detecting a deviation from readings taken at the initial position. Alternatively, automatically monitoring tube 106 movement by system 100 may aid in initially positioning of tube 106 during intubation. Suitable signal analysis methods may be used. For example, the location of internal probe 102 relative to external probes 104 may be monitored and compared to a calibrated and/or expected value indicative of the correct position of tube 106 (which may be confirmed, for example, by x-ray, lung auscultation and/or other method). Deviations away from the calibrated value may be displayed or outputted, to help guide positioning of tube 106.

Alternatively or additionally, correct initial tube 106 positioning within the patient lumen and/or movement of tube 106 within the patient lumen may be detected and/or monitored by measuring ventilation in the lung (e.g., the lobes or any part or parts thereof). Symmetrical lung ventilation (potentially after discounting natural asymmetry due to the differences between the lungs, such as the location of the heart, number of lobs and the like) may be suggestive of proper tube 106 position. Changes from symmetrical to asymmetrical positioning may be suggestive of tube 106 migrational movement.

Optionally, air content is estimated and/or determined. Alternatively or additionally, water content is estimated and/or determined. The air and water content may each or both be estimated together through a relationship, for example, as percent water content plus percent air content theoretically equals one hundred percent (based on a simplification which excludes solids). A change in the air and/or water level may be estimated, for example, by detecting a change or trend in measured values, optionally without estimating an absolute value for either water or air content. Optionally, the air and/or water content is estimated by an air/water measuring module 210C and/or processing unit 202. Measuring the air and/or water content may help detect the presence of medical complications and/or complications due to mechanical ventilation, such as the presence of free air in undesired body regions and/or the presence of water in undesired body regions. It is noted that water may refer to body fluids that contain water, including one or more of stomach acid, pus, blood, exudates, transudates, and/or other fluids. Optionally, the air and/or water content is monitored over time, for example, to detect progression of a complication and/or healing.

Optionally, the presence of air is detected and/or estimated in undesired body locations. Presence of excess air (e.g., free air, or air pockets) may suggest medical complications such as due to air escaping from an injured lung, and/or air that entered the chest cavity from the outside through a wound. For example, the presence of air in the chest cavity outside the lung (pneumomediastinum), collapse of the lung (pneumothorax), air in the abdomen (pneumoperitoneum), air in between the pericardium wall and the heart (pneumopericardium), and/or air in any other undesired location(s). The presence of air in these and other locations may be detected by suitable placement of external probe 104, for example, on the abdomen to detect pneumoperitoneum, or near the heart, to detect pneumopericardium.

Optionally, one or more of internal probe(s) 102 and external probe(s) 104 may be used to transmit an RF signal and receive the transmitted signal locally (e.g., the antenna or plurality of adjacent antennas being on the same side of a sensed region are used transmit a signal and receive its reflection). Such readings may be used to assess the sensor's proximate tissue, and unexpected changes to such signals may indicate for example dislocation of the probe and/or inflammation and/or bleeding or local edema and/or air trapped, in the probe's vicinity, and the like. This may be performed periodically and/or on demand. For example, when presence of air or fluid is detected and/or estimated in undesired body locations, one or more probes that are in the relevant vicinity may be activated in order to locate and/or identify the location and cause of the detected abnormality.

Alternatively or additionally, presence of water is estimated and/or detected in undesired body locations. Presence of body fluids containing mostly water may suggest medical complications that may be due to mechanical ventilation and/or wounds or other conditions. For example, excess fluid in the lungs may suggest pneumonia, bronchitis, congestive heart failure, the presence of blood, pus and/or infective infiltrates, or other sources. Excess fluid outside the lungs may suggest a pleural effusion. Different fluids may be differentiated from each other based on the signal readings, for example, exudates and transudates may be differentiated according to differences in their dielectric properties. Excess stomach acid in the esophagus may suggest reflux.

Excess lung water may be detected, for example, in babies. Detection of excess water may help diagnose certain medical complications in infants. Babies may be under the age of 12 months, and/or under the age of 6 or 3 months and/or newborns or neonates up to the age of 28 days, and/or premature babies that are neonates or older, up to a corrected age of about 6 or 3 months or up to the a corrected age of about 12 months. Babies or neonates having pulmonary congestion and/or related complications may be monitored, for example in cases involving one or more of the following:

Transient Tachypnea of the Newborn (TTN), for example as the result of residual amniotic fluids in the neonatal lungs, potentially causing hypoxemia and tachypnea. The level of amniotic fluid in the lungs may be estimated and/or monitored.

Respiratory Distress Syndrome (RDS), for example due to developmental insufficiency of surfactant production and/or structural immaturity of the lungs. This may result in an exudative infiltration within the lungs (a protein rich fluid) causing hypoxemia. The ventilation of the baby may be estimated and/or monitored. The level of exudative infiltration within the lungs may be estimated and/or monitored.

Patent Ductus Arteriosus (PDA), which may lead to cardiogenic pulmonary edema. The level of pulmonary edema in the lungs may be estimated and/or monitored.

Bronchopulmonary dysplasia (BPD), for example in case of babies who received prolonged mechanical ventilation to treat RDS. Ventilation of the lungs may be estimated and/or monitored, with optional feedback to adjust the ventilation machine. The monitoring and adjustment may reduce or prevent BPD.

Congenital heart disease, including for example, valve defects causing pulmonary congestion. Fluid in the lungs secondary to congenital heart disease may be estimated and/or monitored.

Side effect of treatments such as for sepsis. Ventilation of the lungs may be estimated and/or monitored, with optional feedback to adjust the ventilation machine. The monitoring and adjustment may reduce or prevent complications of treatment.

Some methods of measuring the air and/or water content are now described. By measuring the delay and/or the attenuation and/or the phase shift of a signal (e.g., shown by arrows 108 on FIG. 1) between internal probe 102 and external probes 104, the permittivity and/or fluid content of the tissue within the RF path between the probes may be deduced. The position of the internal probe (e.g., middle (side to side) of thorax) may increase the probability of the signal path as being a direct geometric path (e.g., which is assumed by the measuring method) as compared to transmitting along essentially the same path using only external probe(s). Calculation may be more accurate and reliable due to the ability to ascertain the direct geometric signal path. The geometric location of the external probes may be defined and/or estimated using any method known in the art, including for example by using imaging modalities. Basic anatomic knowledge may be integrated to calculate parameters such as fluid and/or air contents for co-radial segments. Based on a similar method, a dynamic measurement of ventilation for each segment may be constructed. In the case of a coronal splice calculation, external probes may be positioned on several locations on each side of the patient thorax (e.g., left and right lateral edges of the thorax). A lobar distinct measurement may be calculated for each lung lobe. By locating the external probes in more than one axial plane and measuring the geometrical distance between planes, multiple 3D measurements, co-radial to the internal probe, may be calculated using a similar algorithm to the algorithm described above. Imaging may be used to calibrate the location of the internal and/or external probes, for example, x-ray and/or CT images of the patient optionally with the probes may be taken. The distances between probes and/or relative locations of probes may be measured from one or more images (and may be used in the calculations below), and/or obtained from an additional 3D positioning system (e.g., 3D module 218 of FIG. 2). The measured values may be correlated with 2D and/or 3D images denoting patient ventilation and/or respiratory cycle, for example as described herein. The water and/or air content may be estimated for example by the following method:

The exponential representation of an RF signal is shown in Equation (1):

$$S21 = A \cdot \exp\left(\frac{2\pi f \cdot \text{Image}(\sqrt{\varepsilon})L}{c}\right) \cdot \exp\left(-j\frac{2\pi f \cdot \text{Real}(\sqrt{\varepsilon})L}{c}\right) \quad (1)$$

Where S21 is the RF signal from internal probe 102 to external probe 104, A is the non-exponential amplitude factor, f is the signal frequency, ε is the relative complex permittivity, c is the speed of light and L is the geometric distance between the transmitting and the receiving sensors.

The speed of light c is a constant and f is known or controlled. The geometric distance L may be measured or estimates, for example as discussed herein. Based on equation (1), ε may be extracted. The phase and/or amplitude may be obtained based on the extracted ε. By measuring the phase in a specific frequency and using equation (2) or a set of phases and its frequency derivative (equation (3)), the real part of the complex permittivity may be extracted.

$$P_{S21} = \frac{2\pi f \text{Real}(\sqrt{\varepsilon_r})L}{c} \quad (2)$$

$$GD = \frac{\text{Real}(\sqrt{\varepsilon_r})L}{c} = \frac{dP_{S21}}{d2\pi f} \quad (3)$$

$P_{S21}$ is the phase of the RF signal in a specific frequency and GD is the group-delay of a set of frequencies.

By using a non-linear mixing model of air and fluid, the fluid fraction ($x_{water}$) of the medium between the sensors may be extracted (equation (4)).

$$\begin{aligned}\text{Re}(\sqrt{\varepsilon_r}) &= \text{Re}(\sqrt{\varepsilon_r})_{water} * \chi_{water} + \text{Re}(\sqrt{\varepsilon_r})_{air} * (1 - \chi_{water}) \quad (4)\\ &= 8.5 * \chi_{water} + 1 * (1 - \chi_{water})\\ &= 7.5 * \chi_{water} + 1\end{aligned}$$

Optionally, an alert is raised through output unit 206 when estimates suggestive of complications are detected as described herein.

Optionally, the estimates and/or accuracy of the estimates are adjusted based on model based solutions, for example, as described in International Patent Application Publication Number WO2009/031150, and/or International Patent Application Publication Number WO2009/031149, which are incorporated herein by reference. Optionally, a model of thorax or a relevant portion thereof provides a basis for estimating a fluid concentration and/or other parameters described herein. Multiple internal and/or external transducers may be used to obtain RF measured information, which may affect the accuracy of measurement. Additionally, ventilation volume or pattern (or other ventilation parameters) measured (or applied) by a ventilation machine and/or known to change over the breathing cycle, may be utilized as a known parameter in the calculation of concentration of fluids and/or for extracting relative and absolute ventilation values and/or other parameters.

For example, measuring derivates, such as rate of volume changes over time, may be used as a basis for calculation of actual volume within the lung. For example, solving for maximal fit under concentration of dV/dt (i.e., change of volume over time) over different lung models may extract and/or improve accuracy of ventilation and/or concentration of the lung's different parts. Using dV/dT may be used as a basis to calculate V(t) maximal fit with additional dimension of t. The model used and discussed herein may be an RF model which may be based on general statistical knowledge, optionally parameterized and/or fitted to each measured user. The model may be extracted from a 2D and/or 3D patient scan, for example, CT or MRI scan.

Additional methods and/or devices for sensing dielectric properties for monitoring and/or diagnosis of a thorax that may be used in conjunction with the methods and/or systems described herein may be found, in International Patent Application Publication Number WO2009/031150, and/or International Patent Application Publication Number WO2009/031149, which are incorporated herein by reference.

Figure 3:
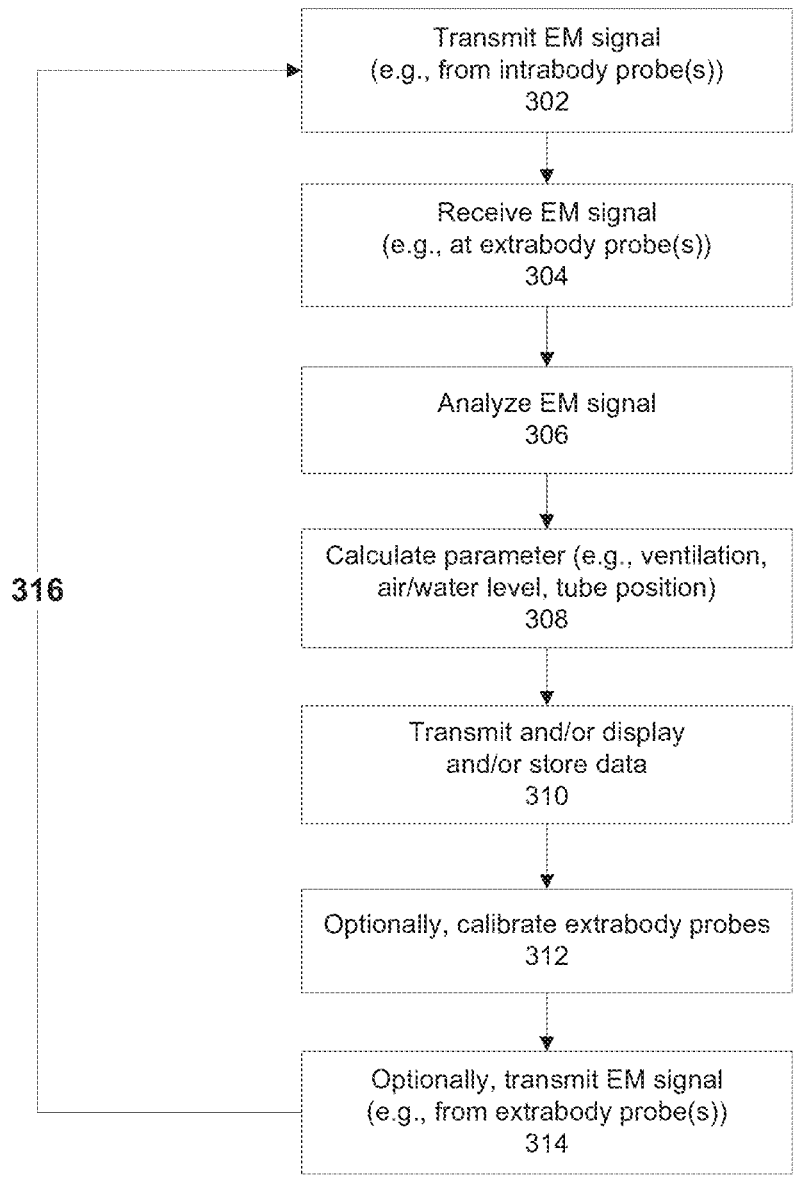
FIG. 3 is a flowchart of a method of monitoring a bodily tissue, for example lung tissue, using a monitoring system, for example as depicted in FIG. 1, in accordance with some embodiments.

Reference is now made to FIG. 3, which is a flowchart of a method for monitoring a bodily tissue, for example lung tissue, for example, using the monitoring system 100 as depicted in FIG. 1, in accordance with some embodiments of the present invention.

Optionally, at 302, an RF signal is generated and transmitted from within a lumen of a patient, such as a trachea and/or esophagus. Alternatively or additionally, the RF signal is generated and transmitted from outside the patient, such as at or near the skin of the patient.

The RF signal may be generated and transmitted by the internal probe and/or the external probe described herein. The internal probe may be coupled to a tube inserted into the patient lumen, such as an endotracheal tube and/or nasogastric tube. The patient may be artificially ventilated via the endotracheal tube.

At 304, the propagated RF signal is received. Optionally, the RF signal is received outside of the body of the patient, at the skin of the patient or in proximity to the skin. The RF signal may be received by the external probe described herein. Alternatively or additionally, the RF signal is received inside the lumen of the patient, such as by the internal probe described herein.

Optionally, multiple internal probes and/or multiple external probes transmit and/or receive RF signals. The probes and/or signal system may be designed to accommodate simultaneous signal transmission and/or reception. All (or some) transducers receiving (and/or transmitting) RF signals may have single and/or multiple RF receiving (and/or transmitting) modules for simultaneous reception of a single transmission and/or for switching between antennas, and/or RF modules for performing time division of the RF modules and/or RF signals between antennas.

At 306, the received RF signals are analyzed, for example, by management unit 110.

Figures 4A, 4B, 4C:
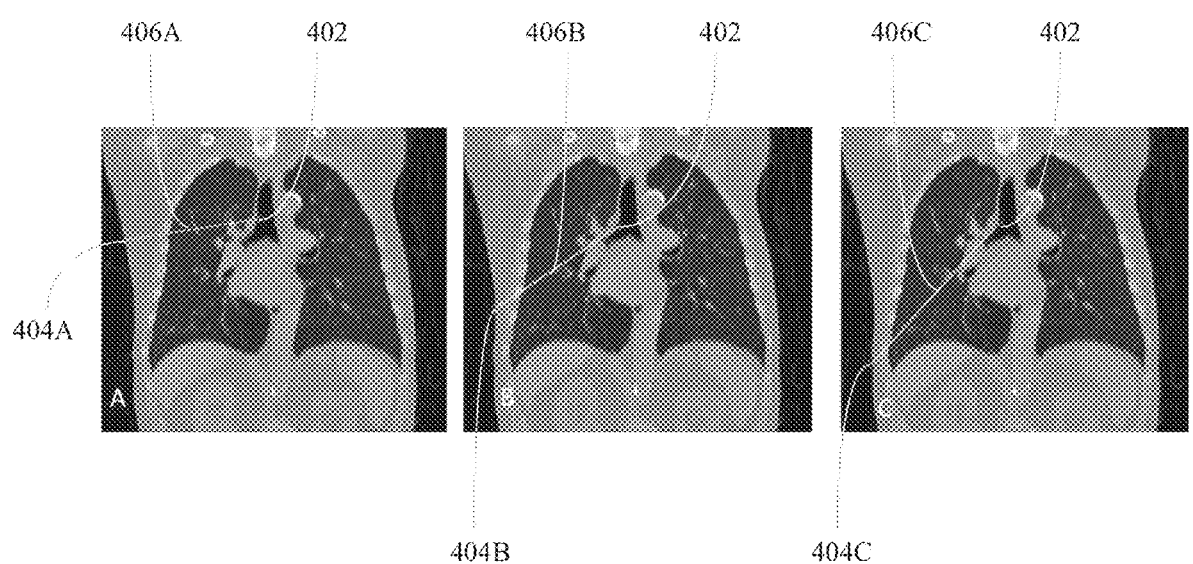
FIGS. 4A-4C are coronal images of the thorax depicting some examples for signal paths for analyzing different sections of lung tissue, in accordance with some embodiments.

Different signals may be analyzed for different lung portions (e.g., different lobes). Reference is now made to FIGS. 4A-4C, which are coronal images (acquired by CT) of the thorax including left and right lung tissue depicting signal paths for analyzing different lung lobes (or other lung parts), in accordance with some embodiments of the present invention. An internal probe 402 is positioned in the trachea, for example, in conjunction with mechanical ventilation of the patient via an endotracheal tube. At FIG. 4A, an external probe 404A is positioned high along the right lateral chest wall relative to the right lung. Signal path 406A between internal probe 402 and external probe 404A may travel only (or mostly) through the upper right lung lobe. At FIG. 4B, an external probe 404B is positioned approximately at the middle of the right lateral chest wall relative to the right lung. Signal path 406B between internal probe 402 and external probe 404B may travel only (or mostly) through the right middle lobe. At FIG. 4C, an external probe 404C is positioned at the lower portion of the right lateral chest wall relative to the right lung. Signal path 406C between internal probe 402 and external probe 404C may travel only (or mostly) through the right lower lobe. In this manner, different lung lobes or portions may be independently and/or separately monitored by the RF signals that uniquely (or mostly) pass through the respective lobe tissue.

Optionally, signals are analyzed at different planes and/or for different locations, such as to form a 2D and/or 3D data set representing the tissue, as described herein.

Referring back to FIG. 3, at 308, biological parameters and/or other parameters are calculated based on the received and/or analyzed RF signals, for example, by management unit 110. For clarity, the analysis of the RF signal as shown at 308 may be optional, as for example the external probe may transmit the data to a remote server for performance of the calculation of the biological parameter.

Optionally, absolute values of the biological parameters are calculated, for example, instantaneous absolute values related to the RF signal. Alternatively or additionally, changes in biological parameters are calculated, for example, trends or changes in values between successive RF signals.

Optionally, ventilation is assessed as described herein. Alternatively or additionally, the position of the tube is assessed as described herein. Alternatively or additionally, fluid content is assessed as described herein. Alternatively or additionally, air content is assessed as described herein.

At 310, the data assessed at block 308 is optionally displayed and/or transmitted and/or stored, as described herein. Optionally, the data is displayed and/or otherwise presented to a user, such as a healthcare worker. For example, indications of medical complications (e.g., alerts) are generated, such as messages sent to the phone of the user, blinking lights, or displayed on a screen.

Data may be transmitted to a ventilation machine or ventilation controller or other server, as described herein.

The data may be acted upon, for example, the ventilation machine may be automatically or manually adjusted based on the data, the position of the endotracheal tube (or other tube) may be adjusted, and/or the patient may be treated.

Blocks 312 and/or 314 described below are optional, and may be performed as additional features in some embodiments of the method and/or system.

Optionally, at 312, the external probes are calibrated based on the internal probe. Signals generated and transmitted only between external probes may be calibrated based on the signals generated and transmitted between the internal probe and the external probe. In this manner, external probes may be used to monitor the tissue without requiring the internal probe.

In some embodiments, the internal probe may be removed or shut down after the calibration process.

Optionally, before removing a ventilation tube, breathing may be evaluated using, for example, external probe(s) to detect autonomic respiration while lowering positive pressure in the ventilation machine. Upon confirmation that breathing is sufficient without external ventilation, the tube may be removed, optionally together with the internal probe(s).

Optionally, at 314, RF signals are generated by external probes. Optionally, the internal probe is not used. Alternatively or additionally, the internal probe receives the generated signals. RF signals may be generated (or reflected) in response to received RF signals. Alternatively or additionally, RF signals are generated independently of the RF signals of block 302, for example, to generate RF signals in a different and/or opposite direction between internal and external transducers.

In this manner, with respect to the method of FIG. 3, different modes of operation are available, such as exclusive use of external probes without the internal probes (after calibration), RF signal propagation from the internal probe to the external probe with optional RF signal propagation return from the external probe to the internal probe, combined RF signal propagation from the internal probe to the external probe and between external probes, RF signal propagation from the external probe to the internal probe (with optional return signal from the internal probe to the external probe), and/or combinations thereof.

Optionally, at 316, monitoring of the tissue continues by generating other RF signals. Monitoring may continue using the internal probe (e.g., block 302) as described herein. The internal probe may be used to send signals and/or to receive signals from the external probe (e.g., block 314). Alternatively, monitoring may continue without the internal probe, when calibration has been performed and signals have been generated by the external probe (e.g., block 314). Examples for monitoring based only on external probes are described, among other things, in International Patent Application Publication Numbers WO2009/031150 and/or WO2009/031149.

Figure 5:
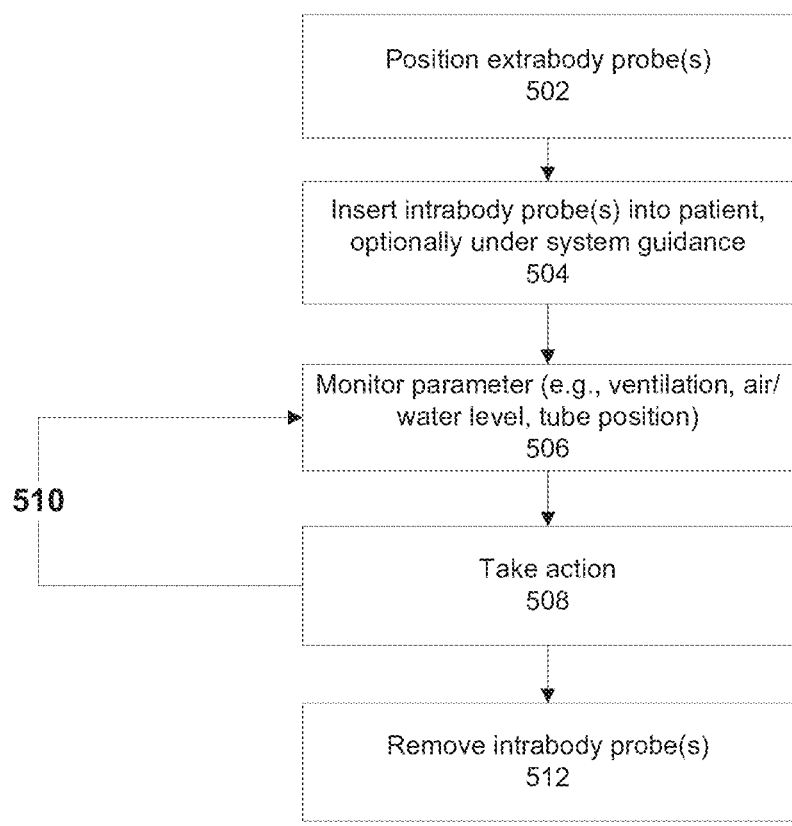
FIG. 5 is a flowchart of a method of using the monitoring system of FIG. 1, in accordance with some embodiments of the present invention.

Reference is now made to FIG. 5, which is a flowchart of a method of using monitoring system 100 of FIG. 1, in accordance with some embodiments of the present invention. System 100 may be used, for example, by a user such as a healthcare professional working to monitoring lungs or parts thereof (or other tissues) of a patient. The patient may be monitored for medical complications (e.g., of intubation and/or mechanical ventilation) and/or disease progression and/or healing.

At 502, external probe(s) are positioned on the skin (or in proximity to the skin) of a patient. For example, the external probes are attached to the skin (or in proximity to the skin) by an adhesive, a vest, a belt, or other methods described herein.

Optionally, the external probes are selectively positioned to monitor different tissue regions, such as different lung lobes or different portions of lungs (e.g., different paths through lungs). The external probes may be positioned to independently monitor the different lung lobes, for example, as discussed with reference to FIGS. 4A-4C above.

Optionally, external probes are selectively placed in order to address spatial resolution and/or attenuation tradeoffs of the received RF signal. Optionally, the types of external probes are selected and/or the external probes are selectively positioned to improve spatial resolution under attenuation conditions during propagation between the internal probe and external probe for different tissues, such as for different lung lobes. For example, at distances further from the internal probe, the RF signal experiences higher attenuation. To get a good reading of the attenuated signal, a larger probe and/or more sensitive probe and/or larger number of probes may be used. The improved reading of the attenuated signal may have a cost of reduced spatial resolution. For example, an error of determining the lung lobe the RF signal traveled through may result. The external probes may be placed taking into account the tradeoff. For example, more sensitive probes may be placed further away from the internal probe.

External probes may be positioned at different parts of the body to monitor different tissues, for example, on the abdomen to monitor for pneumoperitoneum or near the heart to monitor pneumocardium.

At 504, an internal probe is inserted into a lumen of a patient, optionally the lumen is continuous with the pharynx, such as the trachea and/or esophagus, and optionally it is hollow and/or air-filled. The internal probe may be inserted as part of a medical procedure, such as intubation (insertion of an endotracheal tube for mechanical ventilation), insertion of a nasogastric tube, and/or other procedures. Optionally, the internal probe is inserted together with the tube, for example, the internal probe being coupled to the tube. Alternatively or additionally, the internal probe is inserted independently, such as using a catheter or guiding sheath, with or without the tube.

Optionally, positioning of the internal probe within the patient lumen is assisted by system 100. As described herein, system 100 may be used to guide and/or verify the position of the tube based on the RF signals transmitted from the internal probe to the external probes.

Optionally, the internal probe is reversibly inserted.

At 506, biological parameter(s) of the patient tissues (e.g., lungs) are estimated and/or monitored by the system. Examples of biological parameters that are monitored are described herein, including: air levels, fluid levels, ventilation, tube location, and/or other parameters. Alternatively or additionally, the position of the tube is monitored for migrational movement within the patient lumen, as described herein.

Optionally, at 508, action is taken based on the monitoring. Optionally, a ventilation machine is adjusted, for example, based on the estimated ventilation parameters. The ventilation machine may be automatically adjusted, and/or manually adjusted by a user, as described herein.

Alternatively or additionally, the tube is adjusted based on its estimated location. The tube may be adjusted manually by the user, and/or automatically such as by a robot or other machine.

Other actions may be taken based on the monitoring. Optionally, based on the monitoring, the patient is referred to evaluation using another modality, for example, CT, MRI, ultrasound imaging and/or x-ray imaging. The patient may be medically treated. For example, when the monitoring suggests excess fluid in the lungs secondary to congestive heart failure (CHF), medication or other medical treatments may be started. When the monitoring suggests excess fluids due to pneumonia or bronchitis, the patient may be administered antibiotics. When the monitoring suggests excess air in certain tissues, the air may be surgically evacuated or followed for natural absorption by the body. Babies with excess fluid in the lungs due to different causes may be monitored for healing progression. When the monitoring suggests excess fluid, such as stomach acid, in the esophagus such as due to reflux, the stomach acid may be reduced by medications.

Optionally, at 510, monitoring is commenced after the action has taken place. The continued monitoring may denote the effect of the action, for example, further action may be required, different action may be required, or no additional action may be required. For example, a patient is treated and monitoring is used to provide feedback for the success of failure of a treatment regime. Optionally, the action includes adjustment of the regime (e.g., medication type and/or dosage), and/or cessation of treatment.

Optionally, at 512, the internal probe is removed or extracted. Optionally, the internal probe is removed by removal of the tube (e.g., in extubation).

The internal probe may be removed, for example, when the patient does not require intubation, treatment with the nasogastric tube, or other reasons.

The internal probe may be removed, for example, after the external probes have been calibrated to perform tissue monitoring without requiring the internal probe, as described herein.

Figure 6:
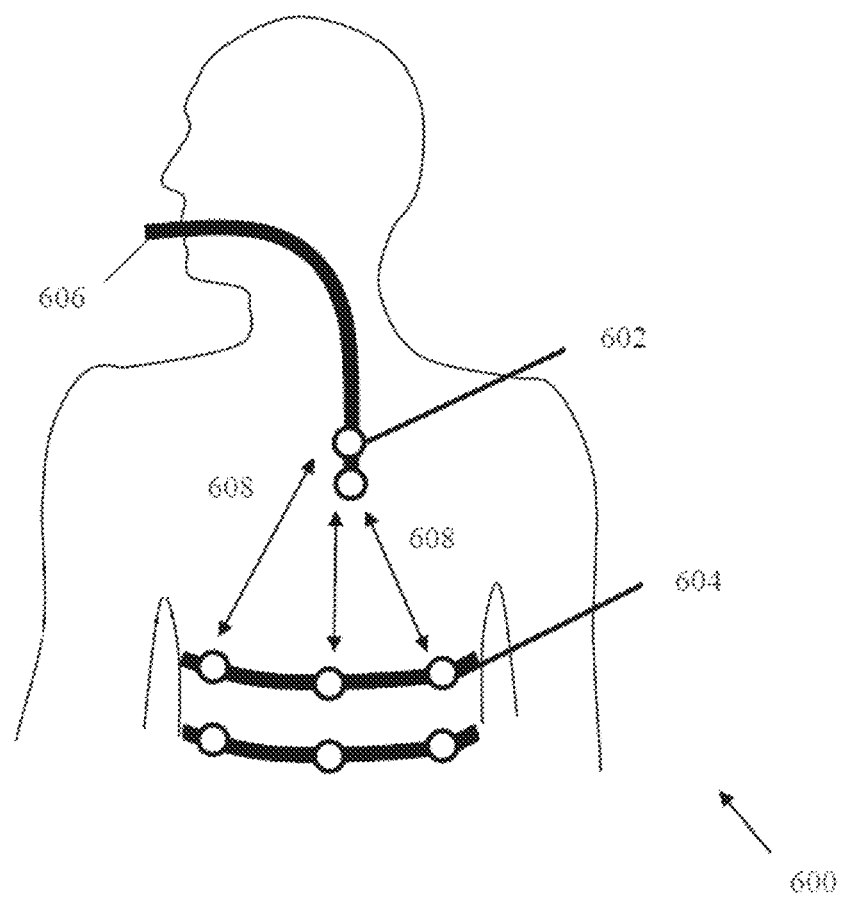
FIG. 6 is a schematic illustration showing an example of an arrangement of internal probe(s) and external probe(s), in accordance with some embodiments.

Reference is now made to FIG. 6, which is a schematic diagram of an arrangement 600 of internal probe(s) 602 and external probe(s) 604, in accordance with some embodiments of the present invention. Optionally, the arrangement is positioned on a patient, optionally a mechanically ventilated patient.

At least one internal probe 602 is positioned within a lumen of a patient using an elongated guiding element 606, for example, within the trachea or esophagus, as described herein.

Multiple external probes 604 are positioned at or near the skin of the patient, as described herein. Optionally, external probes 604 are positioned around the circumference of the body. External probes 604 may be positioned in a ring-like arrangement. There may be one ring, or 2, 3, 4 or more rings (shown are two rings, for example). The ring may encompass about 90 degree, or about 180 degrees, or about 270 degrees, or about 360 degrees, or other arc lengths around the thorax essentially as shown. External probes 604 may be positioned to measure values within: one lung, both lungs, a certain lung lobe, several lung lobes, or other body tissues. External probes 604 may be arranged in other patterns, such as checkerboard.

External probes 604 communicate with internal probe(s) 602 using RF signals as described herein. Signals 608A may travel from external probe 604 to internal probe 604. Signals 608B may travel from internal probe 602 to external probe 604.

It is expected that during the life of a patent maturing from this application many relevant systems and methods will be developed and the scope of the terms internal probe, external probe, and management unit are intended to include all such new technologies a priori. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this present invention may be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the present invention, which are, for clarity, described in the context of separate embodiments, may also be provided in combination in a single embodiment. Conversely, various features of the present invention, which are, for brevity, described in the context of a single embodiment, may also be provided separately or in any suitable subcombination or as suitable in any other described embodiment of the present invention. Certain features described in the context of various embodiments are not to be considered essential features of those embodiments, unless the embodiment is inoperative without those elements.

Although the present invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for estimation at least one dielectric property of tissue of a patient, comprising:
at least one internal probe for at least one of transmitting and receiving an RF signal, the at least one internal probe is set to be mounted on an elongated guiding element set for insertion via the pharynx into a tract of a patient, the at least one internal probe and elongated guiding element are configured to be directly inserted into the tract independently of another guiding device;
at least one external probe which is set to be positioned in a location outside the body for at least one of transmitting and receiving an RF signal;
a processing unit configured to analyze an RF signal transmitted between at least one transducer of the at least one internal probe and at least one transducer of the at least one external probe, propagating via at least one tissue of the patient between walls of the tract and a skin layer of the patient, to estimate at least one dielectric property of the at least one tissue;
a ventilation analysis unit for electrical communication with the processing unit and with a ventilation machine programmed to ventilate the patient according to patient ventilation patterns, the ventilation machine generates signals indicative of the patient ventilation patterns, the processing unit correlates the RF signal denoting sensed ventilation patterns with the received patient ventilation patterns, to compare actual ventilation patterns in the patient tissue with desired ventilation patterns programmed for delivery by the ventilation machine;
wherein the processing unit analyzes the RF signal to detect excess stomach acid in an esophagus of the patient;
wherein the RF signal is unsuitable for generating anatomical images of the at least one tissues.

2. The system of claim 1, comprising an output unit configured to output the at least one dielectric property.

3. The system of claim 2, wherein the output unit is configured to output the at least one dielectric property in a spatial pattern corresponding to an anatomical arrangement of the at least one tissue, the spatial pattern being unsuitable for generating an anatomical image of the at least one tissue.

4. The system of claim 1, wherein the at least one internal probe includes insulation material configured to protect the at least one internal probe again damage from body fluids within the tract.

5. The system of claim 1, wherein the elongated guiding element is a solid rod configured for navigation within the pharynx and the tract.

6. The system of claim 1, wherein the processing unit additionally analyzes the RF signal to estimate a change in a fluid level of the at least one tissue.

7. The system of claim 1, wherein the processing unit additionally analyzes the RF signal to estimate a change in an air level of the at least one tissue.

8. The system of claim 1, wherein the processing unit analyzes the RF signal to estimate migrational movement of the at least one internal probe within the patient tract denoting migrational movement of at least one of an endotracheal tube within the trachea and a nasogastric tube within the stomach.

9. The system of claim 1, wherein the at least one internal probe includes an antenna and the at least one external probe includes an antenna.

10. The system of claim 9, wherein one or both antennas are a dipole antenna.

11. The system of claim 1, wherein the RF signal has a frequency between about 300 Megahertz (MHz) and about 10 Gigahertz (GHz).

12. The system of claim 1, wherein the frequency of the RF signal is selected to improve spatial resolution under higher attenuation during propagation from the at least one internal probe positioned in the tract, through the at least one tissue, to the at least one external probe.

13. The system of claim 1, wherein the processing unit analyzes the RF signal to detect and/or monitor the abnormal presence of air in undesired body locations.

14. The system of claim 1, wherein the processing unit registers at least one parameter calculated from the at least one external probe to 2D or 3D images of the at least one tissue during a respiration cycle.

15. The system of claim 1, wherein the processing unit analyzes the RF signal to assess lung ventilation through the at least one tissue.

16. The system of claim 15, wherein lung ventilation is assessed for one or both of symmetrical ventilation between the left and right lung, and for adequate ventilation to at least one lung lobe.

17. The system of claim 15, wherein lung ventilation is individually assessed for different lung lobes based on RF signals traveling through each respective lung lobe.

18. The system of claim 15, wherein the processing unit generates a signal for adjusting the ventilation machine; wherein the ventilation machine is a mechanical ventilation machine ventilating the patient based on the assessed lung ventilation; wherein the generated signal is transmitted to at least one of a monitor for display to a user and a ventilation controller of the mechanical ventilation machine for automatically adjusting the mechanical ventilation machine.

19. A system for estimation at least one dielectric property of tissue of a patient, comprising:
    at least one internal probe for at least one of transmitting and receiving an RF signal, the at least one internal probe is set to be mounted on an elongated guiding element set for insertion via the pharynx into a tract of a patient, the at least one internal probe and elongated guiding element are configured to be directly inserted into the tract independently of another guiding device;
    at least one external probe which is set to be positioned in a location outside the body for at least one of transmitting and receiving an RF signal;
    a processing unit configured to analyze an RF signal transmitted between at least one transducer of the at least one internal probe and at least one transducer of the at least one external probe, propagating via at least one tissue of the patient between walls of the tract and a skin layer of the patient, to estimate at least one dielectric property of the at least one tissue;
    a mechanical ventilation machine interface for electrical coupling to a mechanical ventilation machine ventilating the patient, the processing unit performing a calibration of RF signals denoting sensed ventilation patterns based on patient ventilation parameters received from the mechanical ventilation machine, the processing unit analyzing the calibrated RF signals for changes in patient ventilation patterns;
    wherein the processing unit analyzes the RF signal to detect excess stomach acid in an esophagus of the patient;
    wherein the RF signal is unsuitable for generating anatomical images of the at least one tissues.

20. A method for estimating at least one biological parameter of tissue of a patient, comprising:
    positioning at least one internal probe configured for at least one of transmitting and receiving an RF signal, via the pharynx into a tract of a patient, the at least one internal probe is set for insertion and retraction from the tract using an elongated guiding element, the at least one internal probe and elongated guiding element are configured to be directly inserted into the tract independently of another guiding device;
    positioning at least one external probe outside the body of the patient in proximity to a skin layer of the patient, the at least one external probe configured for at least one of transmitting and receiving an RF signal;
    propagating the RF signal via at least one tissue between at least one transducer of the at least one internal probe and at least one transducer of the at least one external probe, the RF signal propagating via at least one tissue of the patient between walls of the tract and the skin layer of the patient;
    analyzing the propagated RF signal to estimate at least one biological parameter of the at least one tissue; and
    outputting the at least one biological parameter;
    wherein the RF signal is unsuitable for generating anatomical images of the at least one tissues;
    wherein the at least one biological parameter comprises at least one ventilation parameter of the at least one tissue, the method further comprising adjusting a ventilation machine based on the at least one measured ventilation parameter, to reduce or prevent ventilation induced lung injury.

21. The method of claim 20, wherein the at least one internal probe is positioned within an esophagus of an intubated patient having an endotracheal tube in the trachea, or wherein the at least one internal probe is positioned within the trachea of a patient having a nasogastric tube positioned within the esophagus.

22. The method of claim 20, wherein the at least one internal probe is positioned within an esophagus of a patient having a nasogastric tube positioned within the esophagus, or wherein the at least one internal probe is positioned within the trachea of an intubated patient having an endotracheal tube in the trachea, the at least one internal probe being positioned next to the nasogastric tube or the trachea.

23. The method of claim 20, further comprising detecting migrational movement of at least one of an endotracheal tube and a nasogastric tube within the tract, the migration movement detected based on analysis of the RF signal transmitted and/or received by the at least one internal probe coupled to the endotracheal tube or the nasogastric tube.

24. The method of claim 20, wherein the RF signal is transmitted by the at least one internal probe and received by the at least one external probe.

25. The method of claim 20, wherein the tract is an esophagus or a trachea.

26. The method of claim 20, wherein the patient is intubated and mechanically ventilated.

27. The method of claim 20, further comprising removing the at least one internal probe from the tract after a measuring session has been completed.

28. The method of claim 20, wherein the at least one tissue includes lung tissue.

29. The method of claim 20, wherein the patient is a baby less than 12 months old.

30. The method of claim 20, further comprising calibrating propagation of RF signals between the at least one external probe via the at least one tissue with analyzed RF signals between the at least one internal probe and the at least one external probe.

31. The method of claim 20, wherein the at least one internal probe and the at least one external probe are positioned to confine an individual lobe of a lung.

32. The method of claim 20, further comprising detecting abnormal levels of at least one of air and water in the at least one tissue.

33. The method of claim 23, further comprising re-adjusting the position of the endotracheal tube to improve patient ventilation.

34. The method of claim 29, wherein the baby is a prematurely born baby.

35. The method of claim 30, further monitoring the at least one biological parameter based only on the propagation of RF signals between the plurality of the at least one external probe.

36. The method of claim 32, further comprising treating a patient medical condition to correct the abnormal level.

37. A method for monitoring a mechanically ventilated patient, comprising:
positioning at least one internal probe within a tract of a patient via the pharynx, using an elongated guiding element, the at least one internal probe configured for at least one of transmitting and receiving an RF signal, the at least one internal probe and elongated guiding element are configured to be directly inserted into the tract independently of another guiding device;
positioning at least one external probe in proximity to a skin layer of the patient, the at least one external probe configured for at least one of transmitting and receiving an RF signal;
receiving applied ventilation pattern signals from a ventilation analysis unit coupled to a mechanical ventilation machine mechanically ventilating the patient;
correlating between the applied ventilation pattern signals and an RF signal propagated via at least one tissue between at least one transducer of the at least one internal probe and at least one transducer of the at least one external probe;
analyzing the correlated signal for monitoring at least one ventilation parameter of the patient; and
outputting the at least one ventilation parameter.

38. The method of claim 37, further comprising adjusting the mechanical ventilation machine ventilating the patient based on the correlated signal.

39. A system for estimating at least one ventilation parameter of a mechanically ventilated patient, comprising:
at least one internal probe set for insertion into a tract of a patient via the pharynx, the at least one internal probe is set to be mounted on a elongated guiding element, the at least one internal probe configured for at least one of transmitting and receiving an RF signal, the at least one internal probe and elongated guiding element are configured to be directly inserted into the tract independently of another guiding device;
at least one external probe which is set to be mounted in an external location for receiving a propagated RF signal, the at least one external probe configured for at least one of transmitting and receiving an RF signal;
a ventilation analysis unit for receiving applied ventilation pattern signals of a mechanical ventilation machine mechanically ventilating the patient;
a processing unit which analyzes a correlation between the applied ventilation pattern signals and an RF signal propagated via at least one tissue between at least one transducer of the at least one internal probe and at least one transducer of the at least one external probe, for monitoring at least one ventilation parameter of the patient; and
an output unit which outputs the at least one ventilation parameter.

40. The system of claim 39, wherein the processing unit performs a calibration of the propagated RF signals based on the applied ventilation pattern signals, the processing unit analyzing subsequent calibrated RF signals for changes in patient ventilation patterns.

41. The system of claim 39, wherein the processing unit generates a signal for adjusting the mechanical ventilation machine ventilating the patient based on assessed lung ventilation denoted by the at least one ventilation parameter, the generated signal transmitted to at least one of a monitor for display to a user and a ventilation controller of the mechanical ventilation machine for automatically adjusting the mechanical ventilation machine.

* * * * *